(12) United States Patent
Chamney et al.

(10) Patent No.: US 11,389,579 B2
(45) Date of Patent: Jul. 19, 2022

(54) APPARATUS FOR PERFORMING PERITONEAL DIALYSIS

(71) Applicant: Fresenius Medical Care Deutschland GmbH, Bad Homburg (DE)

(72) Inventors: Paul Chamney, Tring (GB); Peter Wabel, Darmstadt (DE); Klaus Wolf, Muedesheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 305 days.

(21) Appl. No.: 16/613,446

(22) PCT Filed: May 16, 2018

(86) PCT No.: PCT/EP2018/062659
§ 371 (c)(1),
(2) Date: Nov. 14, 2019

(87) PCT Pub. No.: WO2018/210904
PCT Pub. Date: Nov. 22, 2018

(65) Prior Publication Data
US 2020/0353148 A1 Nov. 12, 2020

(30) Foreign Application Priority Data
May 16, 2017 (EP) .................... 17171392

(51) Int. Cl.
*A61M 1/16* (2006.01)
*A61M 1/28* (2006.01)
*B01D 61/32* (2006.01)

(52) U.S. Cl.
CPC .......... *A61M 1/282* (2014.02); *A61M 1/1601* (2014.02); *B01D 61/32* (2013.01);
(Continued)

(58) Field of Classification Search
CPC ................ A61M 1/282; A61M 1/1601; A61M 2205/3348; A61M 2205/3351;
(Continued)

(56) References Cited

U.S. PATENT DOCUMENTS 5,004,459 A 4/1991 Peabody et al.
5,670,057 A * 9/1997 Chen .................... A61M 1/1609
210/252

(Continued)

FOREIGN PATENT DOCUMENTS

WO WO 2016/095026 6/2016

OTHER PUBLICATIONS

Agnes Dejardin et al, "Intraperitoneal pressure in PD patients: relationship to intraperitoneal volume body size and PD-related complications", Published in Nephrol Dial Transplant (2007), vol. 22, pp. 1437-1444, published Feb. 17, 2007. (Year: 2007).*

*Primary Examiner* — Joseph W Drodge
(74) *Attorney, Agent, or Firm* — Jacobson Holman PLLC

(57) ABSTRACT

The present invention relates to an apparatus for performing peritoneal dialysis, the apparatus comprising means for delivering dialysis fluid to the peritoneal cavity of a patient, a measurement device for measuring the fluid pressure of the delivered dialysis fluid and/or the fluid pressure in the peritoneal cavity, i.e. the intraperitoneal pressure and/or any pressure related thereto, and a control unit operably connected to said means and the measurement device, wherein the control unit is configured to effect an inflow or outflow phase encompassing a series of fill-and-measurement or drain-and-measurement steps, each step comprising delivering a predetermined quantity of dialysis fluid to the peritoneal cavity or draining a predetermined quantity of dialysis fluid from the peritoneal cavity and subsequently measuring and recording a pressure value.

16 Claims, 13 Drawing Sheets

Figure 1:
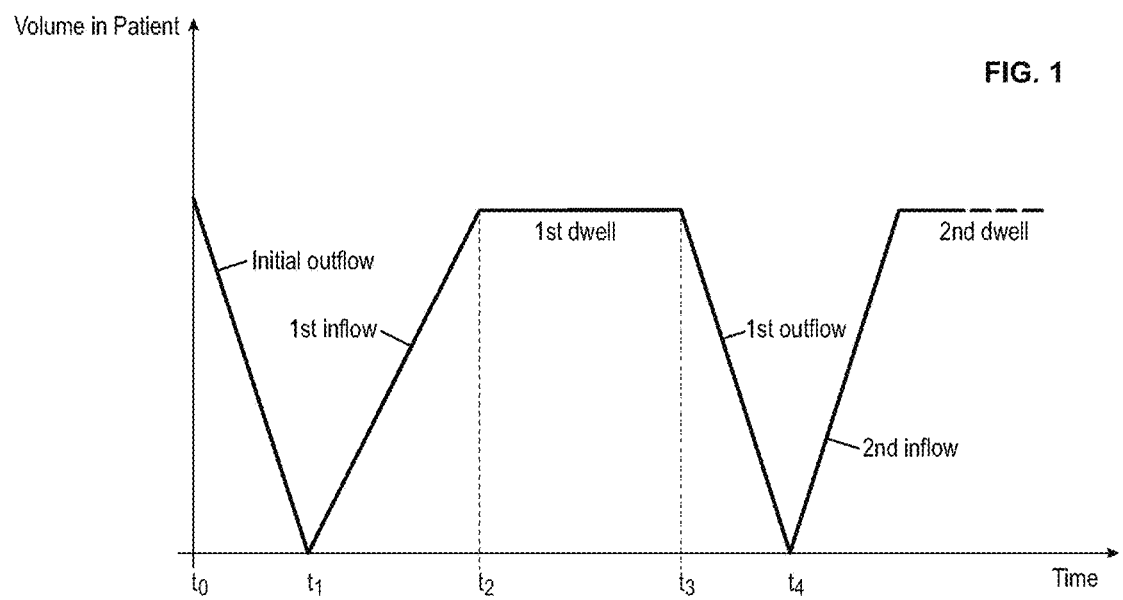

(52) U.S. Cl.
CPC .............. *A61M 2205/3348* (2013.01); *A61M 2205/3351* (2013.01); *A61M 2230/005* (2013.01)

(58) Field of Classification Search
CPC ............ A61M 2230/005; A61M 1/281; A61M 2205/50; A61M 2205/52; A61M 1/28; A61M 1/1603; A61M 1/1615; A61M 1/1617; A61M 2205/3331; A61M 2205/3334; A61M 2205/3341; B01D 61/30; B01D 61/32
See application file for complete search history.

(56) References Cited

U.S. PATENT DOCUMENTS

| | | | |
|---|---|---|---|
| 6,228,047 B1 | 5/2001 | Dadson | |
| 2009/0198174 A1* | 8/2009 | Childers | A61M 1/282 604/29 |
| 2010/0004590 A1* | 1/2010 | Hedmann | A61M 1/28 604/29 |
| 2010/0191180 A1* | 7/2010 | Childers | A61M 1/282 604/29 |
| 2010/0191181 A1* | 7/2010 | Childers | B01D 61/32 604/29 |
| 2014/0018727 A1 | 1/2014 | Burbank et al. | |
| 2015/0005699 A1* | 1/2015 | Burbank | A61M 1/28 604/29 |
| 2016/0101227 A1* | 4/2016 | Norris | A61M 1/3656 604/29 |
| 2016/0216150 A1* | 7/2016 | Groeber | A61M 1/282 |
| 2018/0043078 A1* | 2/2018 | Gerber | A61M 1/1613 |
| 2018/0193546 A1* | 7/2018 | Gerber | A61B 5/14507 |

* cited by examiner

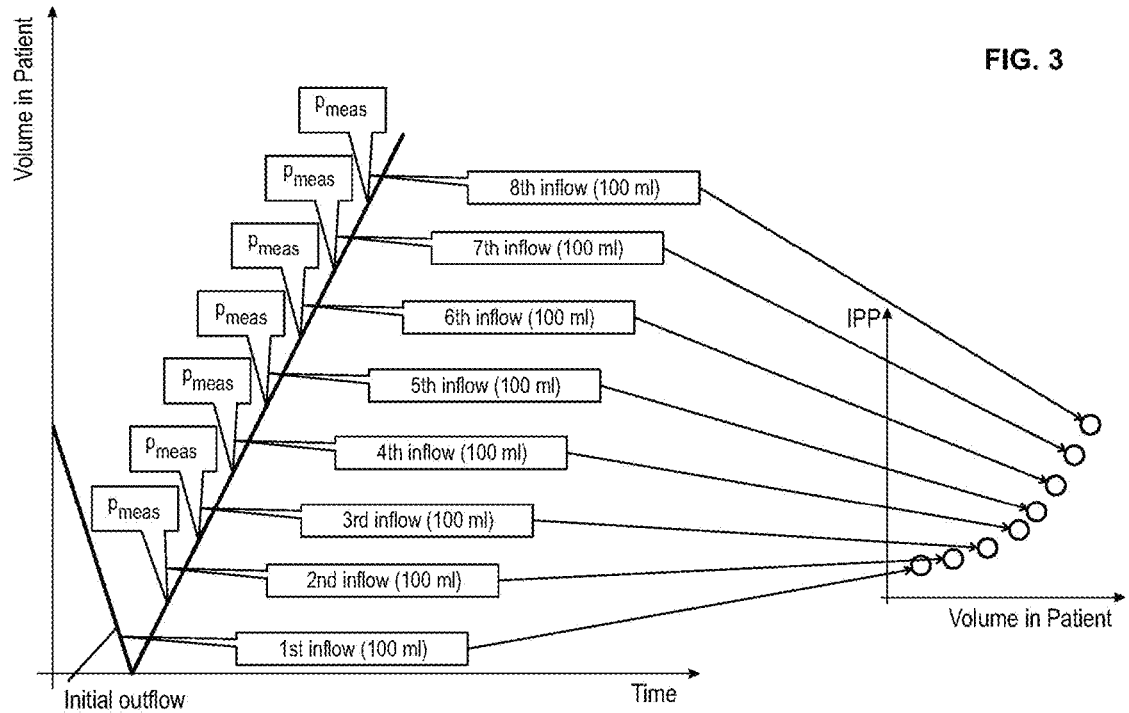
FIG. 3
FIG. 4
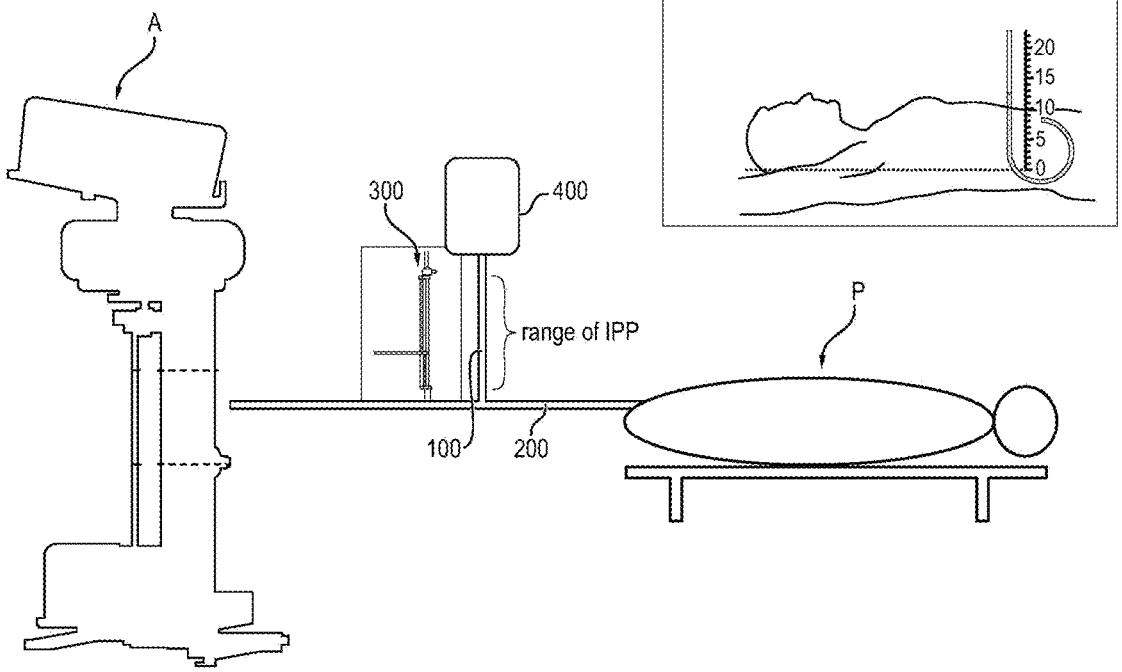

APPARATUS FOR PERFORMING PERITONEAL DIALYSIS

The present invention relates to an apparatus for performing peritoneal dialysis.

In peritoneal dialysis, a dialysis solution is run through a tube into the peritoneal cavity, the abdominal body cavity around the intestine. The peritoneal membrane acts as membrane for removing waste and excess water from the blood. The therapy comprises cycles of dialysis fluid inflow, dwell and dialysis fluid outflow. Automatic systems can run a series of cycles overnight. Peritoneal dialysis can be carried out at a patient's home and frees patients from the routine of having to go to a dialysis clinic on a fixed schedule multiple times per week.

Automatic systems (APD) perform all or at least a part of the steps for performing the treatment automatically, i.e. without interaction by a user. The present invention, however, is not restricted to those systems but also encompasses peritoneal dialysis machines which require user interaction.

Further there are peritoneal dialysis machines in which one or more pumps are used for moving the dialysis fluid as well as peritoneal dialysis machines without such pumps and combinations of those types of machines. Peritoneal dialysis machines without pumps are gravity driven, i.e. the movement of the dialysis fluid is caused by gravity. The present invention encompasses all those and other conceivable types of peritoneal dialysis machines.

Not all patients are eligible for peritoneal dialysis therapy or can receive peritoneal dialysis therapy over unlimited periods, because peritoneal dialysis is less efficient than hemodialysis and because peritoneal membrane function can decline over time. There is hence a need to maximize therapy efficiency and minimize peritoneal membrane function decay. Apart from optimizing compositions of peritoneal dialysis fluids, this can be achieved by optimizing therapy parameters, such as filling volumes, dwell times, number of fluid exchanges and so forth.

The present invention aims to provide an apparatus for performing peritoneal dialysis, which implements a routine to support an optimization of therapy parameters and hence maximize therapy efficiency and minimize peritoneal membrane function decay.

Against this background, the invention pertains to an apparatus for performing peritoneal dialysis, the apparatus comprising means for delivering dialysis fluid to the peritoneal cavity of a patient, a measurement device for measuring the fluid pressure of the delivered dialysis fluid and/or the fluid pressure in the peritoneal cavity (intraperitoneal pressure) and/or any pressure related thereto, and a control unit operably connected to the said means and the measurement device, wherein the control unit is configured to effect an inflow or outflow phase encompassing a series of fill-and-measurement steps or drain-and-measurement steps, each step comprising delivering a predetermined quantity of dialysis fluid to the peritoneal cavity or draining a predetermined quantity of dialysis fluid from the peritoneal cavity and subsequently measuring and recording a pressure value, or encompassing a continuous inflow or outflow of dialysis fluid to or from the peritoneal cavity and a measurement routine where pressure values are recorded during in- or outflow of the dialysis fluid, or encompassing a semi-continuous routine which is a combination of both, or to effect a dwell phase and a pressure measurement during dwell, to establish a function of intraperitoneal pressure by added volume or absolute intraperitoneal volume and to use this function to generate and output at least one therapy-related prediction or recommendation.

Said means for delivering dialysis liquid may comprise one or more pumps, hoses, valves etc. However, the present invention also encompasses dialysis devices without pumps, i.e. gravimetric cycler. In that case said means are hoses, valves etc. and the flow of dialysis liquid into and/or out of the peritoneal cavity is caused by gravity.

Preferably the control unit is adapted so that the measurement and/or recordal of the pressure value is made at idle pump or in case of gravimetric cyclers when no fluid is flowing into and out of the patient.

According to the invention, the control unit is able to establish a function of pressure by added volume and to use this function to determine at least one patient-specific characteristic, which forms the basis for a prediction of recommendation to be given on the peritoneal dialysis therapy. The function of pressure by added volume will be a non-linear function of typically increasing slope, i.e., convex shape, meaning that the pressure increase per added volume will grow with the overall filling volume. The increase in slope is because of the increasing peritoneal membrane counterpressure. The function will be characteristic of a patient's volume of the peritoneal cavity and of the condition of the peritoneal membrane. It can be used, in conjunction with predetermined empirical values, to output certain therapy-related predictions or recommendations.

In one embodiment, the control unit is configured to establish a relationship of IPP (Interperitoneal pressure) to IPV (Interperitoneal volume) and to analyse this relationship to obtain prediction parameters for the at least one therapy-related prediction or recommendation. For example, the IPP measurement can be used to output therapy-related predictions or recommendations based on one or more of the following assessments: drain optimisation to afford better control of UF, means to track changes in fluid status, greater visibility to peritoneal cavity drainage issues, early warning detection of peritonitis, determination of the average hydraulic conductance (UF coefficient) of the peritoneal membrane (a major factor in the delivered UF), an online frequent tracking of peritoneal membrane function and a tracking of aquaporin loss and EPS progression.

The dialysis machine or any other storage medium may be adapted to store a patient individual IPP (interperitoneal pressure) tolerated/comfort value. This is a specific IPP which the patient tolerates. This value can be used for the next measurement of IPP not to exceed the value within the IPP measurement.

It is also conceivable to use this value in case of a IPP guided treatment as a maximum value. In that case the IPP does not exceed this default value during a normal treatment.

The measuring device can be an integrated part of the pump or of any part of the dialysis machine or can be a separate device.

It can be a sensor such a separate sensor within the patient line, e.g. a membrane based disposable pressure sensor. In that case the patent line (hose) comprises an area with increased flexibility and the displacement of the area is indicative for the pressure in the line. It is possible and encompassed by the invention to connect a specific membrane based pressure sensor to the disposable (tubing) of this specific test sequence.

In one embodiment, the therapy-related recommendation is at least one of the optimum filling volume for dialysis fluid in the peritoneal cavity, the optimum dwell time or the optimum amount of inflow-dwell-outflow cycles. With the aid of predetermined empirical values, the function of pressure by added volume can be used to output such recommendations. The parameters of filling volume, dwell times and amount of cycles within one therapy session stand in connection with therapy efficiency and long term peritoneal membrane function decay.

In one embodiment, the therapy-related prediction is at least one of the overall therapy time or the ultrafiltration volume. With the aid of predetermined empirical values, the function of pressure by added volume can be used to output such predictions, which are useful in improving therapy control and patient comfort.

In one embodiment, the control unit is configured to start the inflow phase after a complete drain of dialysis fluid from the peritoneal cavity. The control unit is hence configured to carry out the inflow phase and more specifically the first fill-and-measurement step after carrying out an (initial) outflow phase, where used dialysis fluid is drained from the patient's peritoneal cavity. In this embodiment, the inflow phase hence starts at a point where the patient's peritoneal cavity is empty, i.e., is not filled with dialysis fluid.

In one embodiment, the control unit is configured to use the first pressure value determined during the first fill-and-measurement step as an offset and to establish the function of pressure by added volume on the basis of all subsequent pressure values determined during the subsequent fill-and-measurement steps or routine, each corrected by subtracting the offset. The first pressure value and first volume increment are hence not used as part of the pressure-by-volume function. The first pressure value is rather subtracted from each subsequent pressure value to obtain corrected values. The corrected values are then used as part of the function. This is because the measured pressure is represented by the sum of the hydrostatic pressure and the intraperitoneal pressure (IPP), with only the intraperitoneal pressure being relevant for the generation of the therapy-related prediction or recommendation herein. When the inflow phase starts at a point where the patient's peritoneal cavity is not filled with dialysis fluid, e.g., is fully drained, the first pressure value can reasonably be assumed to be very close to the hydrostatic pressure, because not enough volume has been filled into the peritoneal cavity to obtain significant IPP, i.e., significant membrane counter-pressure, but the fluid level will already approximate its final level.

In one embodiment, when applying fill-and-measurement steps or drain-and-measurement steps, the control is configured to deliver or drain the same quantity of dialysis fluid to and from the peritoneal cavity in all cycles. Exemplary quantities are between 20 and 200 ml, preferably between 50 and 150 ml and more preferably between 80 and 120 ml. In another embodiment, the quantity varies with each cycle, e.g., becomes smaller by a certain increment with each subsequent cycle.

In one embodiment, when applying fill-and-measurement steps or drain-and-measurement steps, the number of fill-and-measurement steps or drain-and-measurement steps is greater five and preferably greater ten. An amount of value pairs of intraperitoneal pressure versus overall filling volume exceeding these numbers allows establishing a conclusive function.

In one embodiment, the control unit is configured to consider dynamic pressure measurements obtained during a fluid inflow or outflow in the inflow or outflow phase during a continuous routine, wherein preferably dynamic pressure effects are considered to correct the pressure values. Static IPP measurement where the IPP-IPV characteristic of the peritoneal cavity is captured by filling the cavity with volume increments then measuring the hydrostatic pressure with the fluid at rest can be time consuming and the resolution of the IPP-IPV characteristic can relatively coarse. Dynamic approaches can offer a solution to this problem.

In one embodiment, the control unit is configured to temporarily slow down the inflow or outflow rate when carrying out dynamic pressure measurements. Such may reduce pressure effects and, if measurements are also carried out at full flow rate or two reduced flow rates, allows to correct such effects when the calculations can be carried out at two different flow rates.

In one embodiment, the control unit is configured to consider both dynamic pressure measurements and static pressure measurements. Such even offers a greater scope for dynamic pressure compensation and compensation for non-laminar flow.

The measurement device may be or comprise at least one sensor. It may also comprise a tube which is connected to the patient catheter, wherein the level of dialysis fluid in said tube is an indicator for the intraperitoneal pressure and wherein the measurement device further comprises means to measure said level.

In one embodiment, the control device is adapted to stop further inflow of dialysis liquid into the peritoneum in case that the intraperitoneal pressure reaches a specific maximum level.

Figure 2:
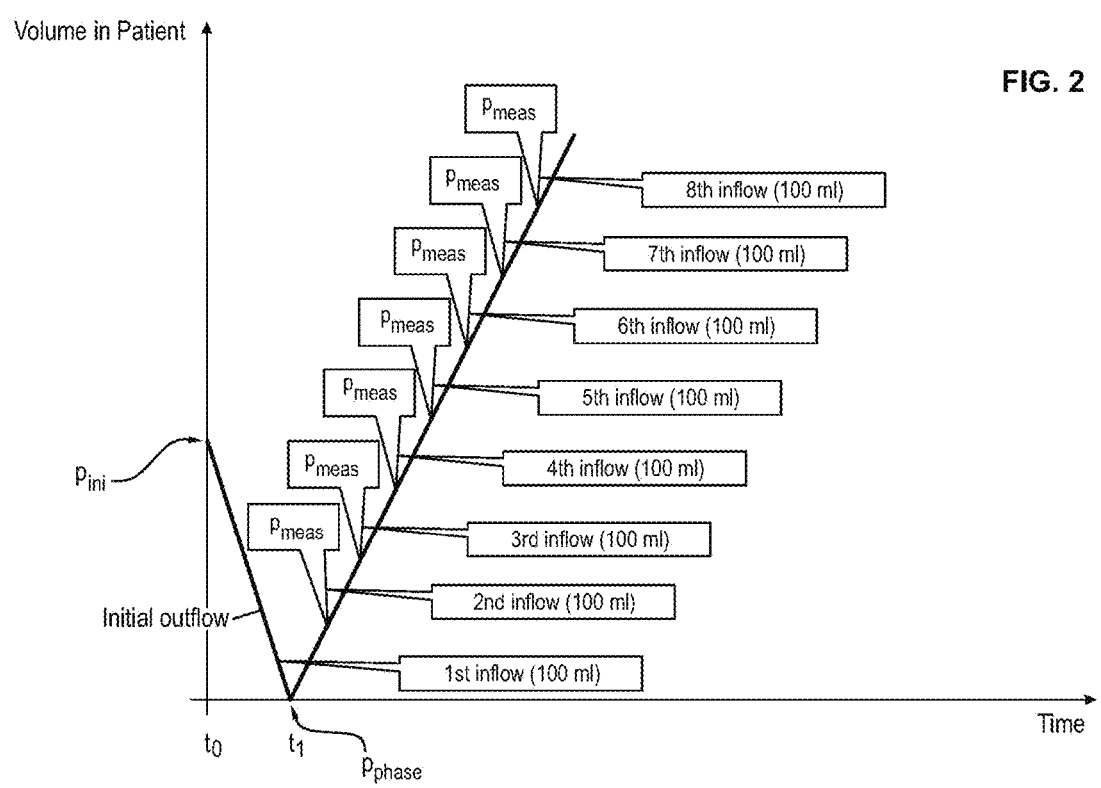
Figure 5:
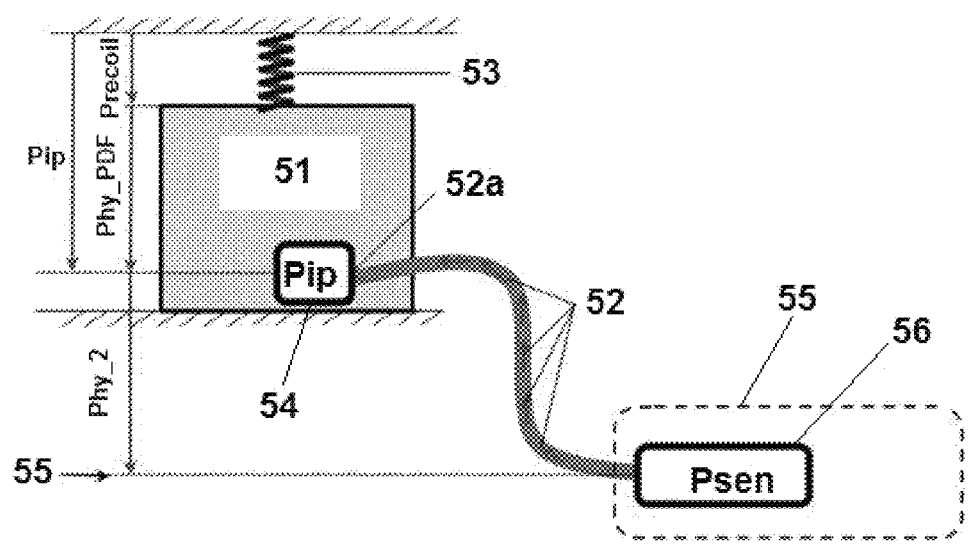
Figure 8:
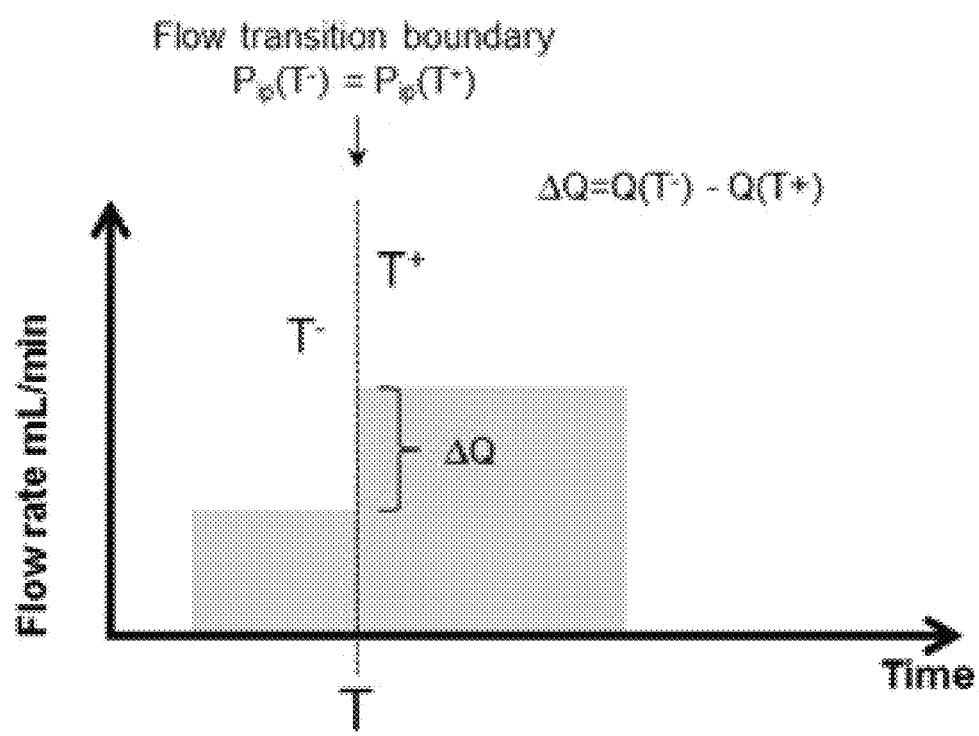
Figure 9:
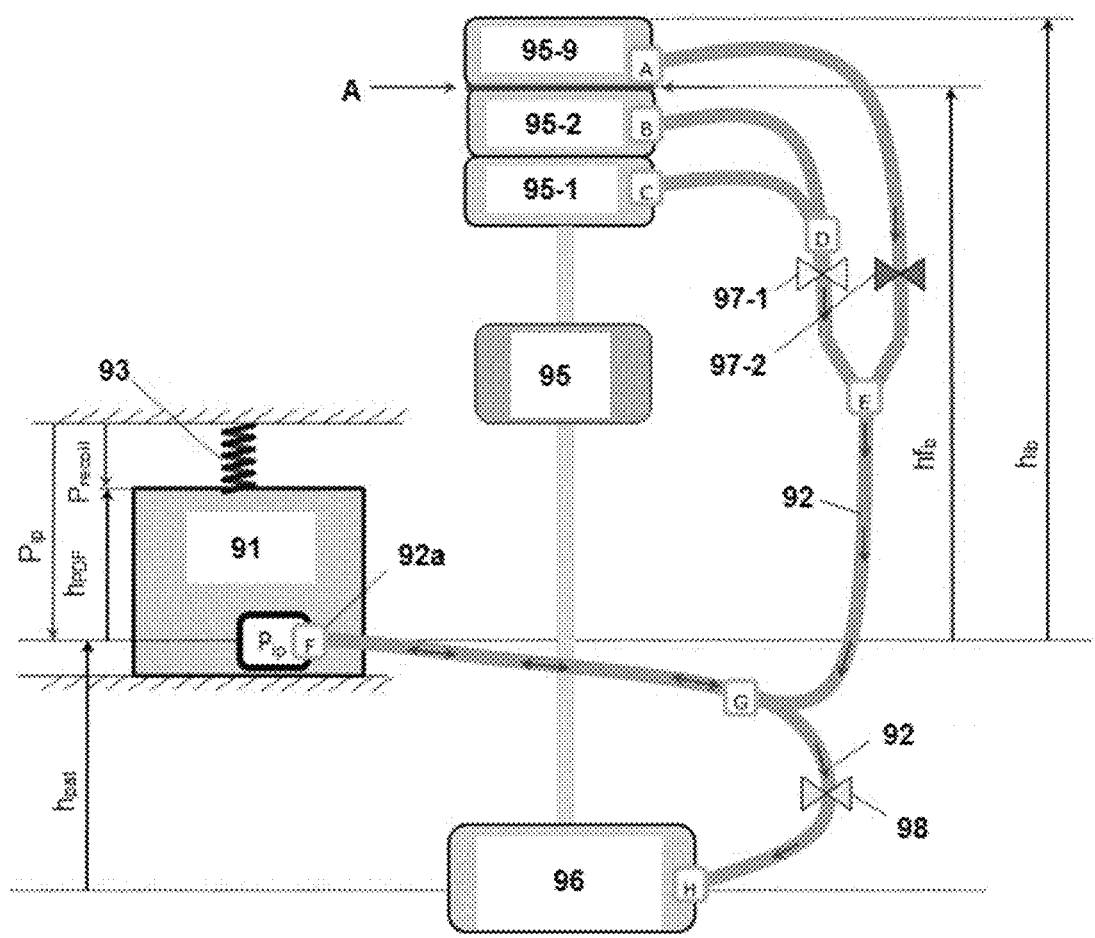
Figure 10:
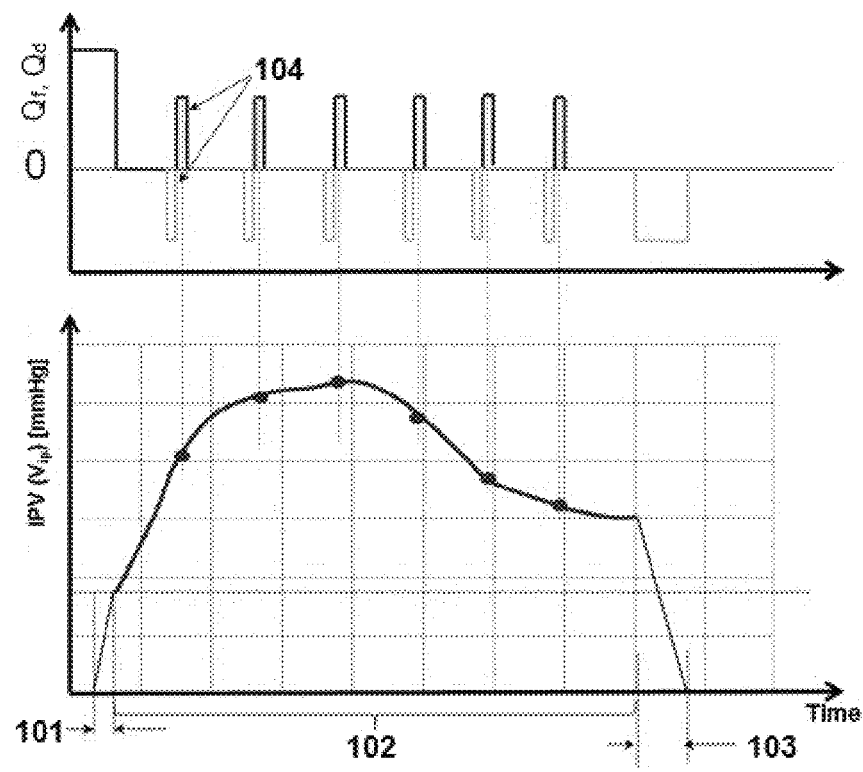
Figure 11:
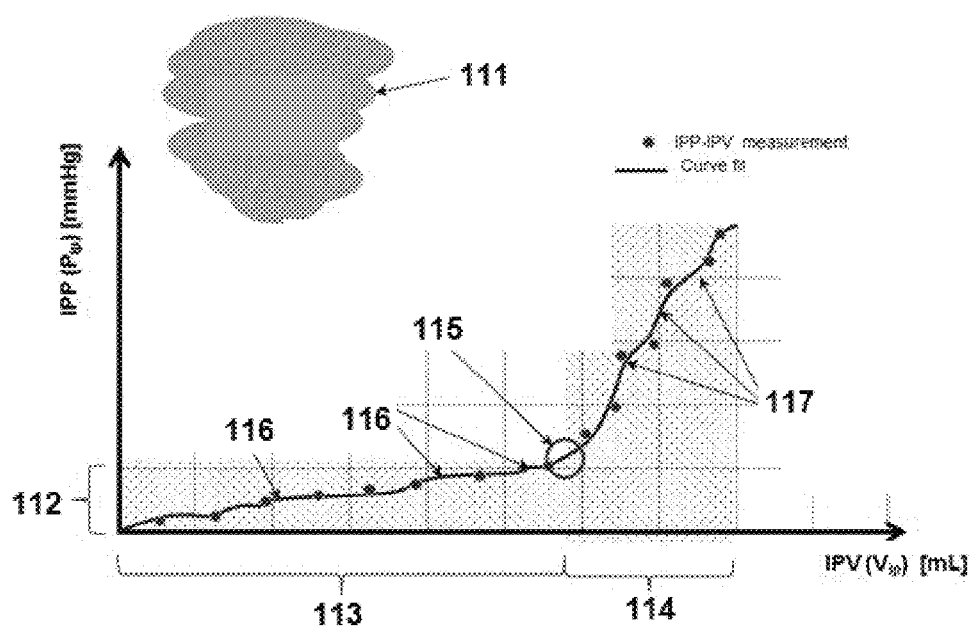
Figure 12:
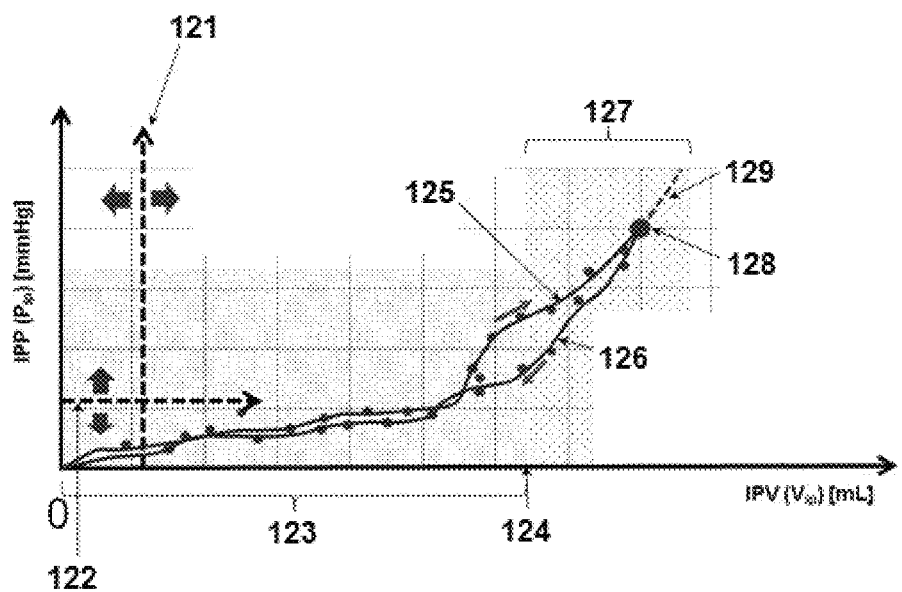
Figure 13:
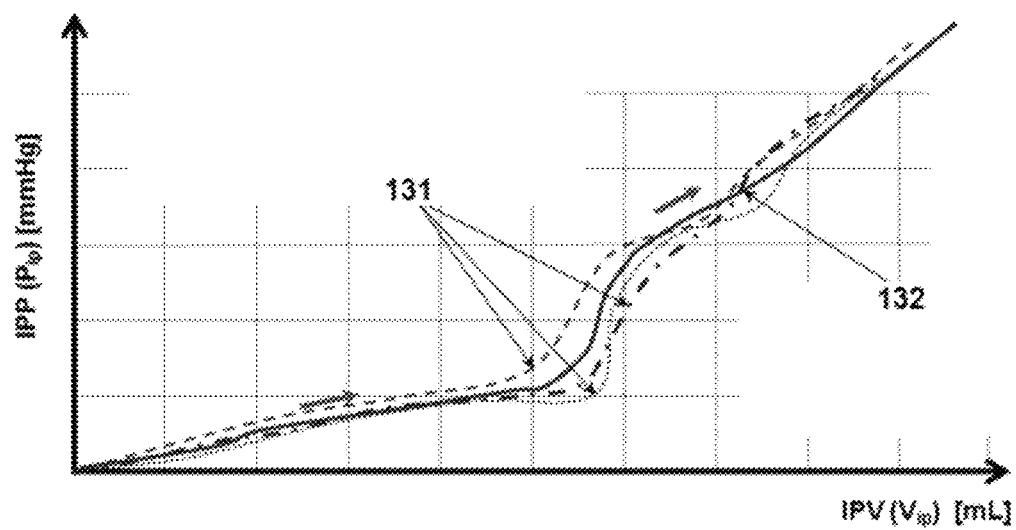
Figure 14:
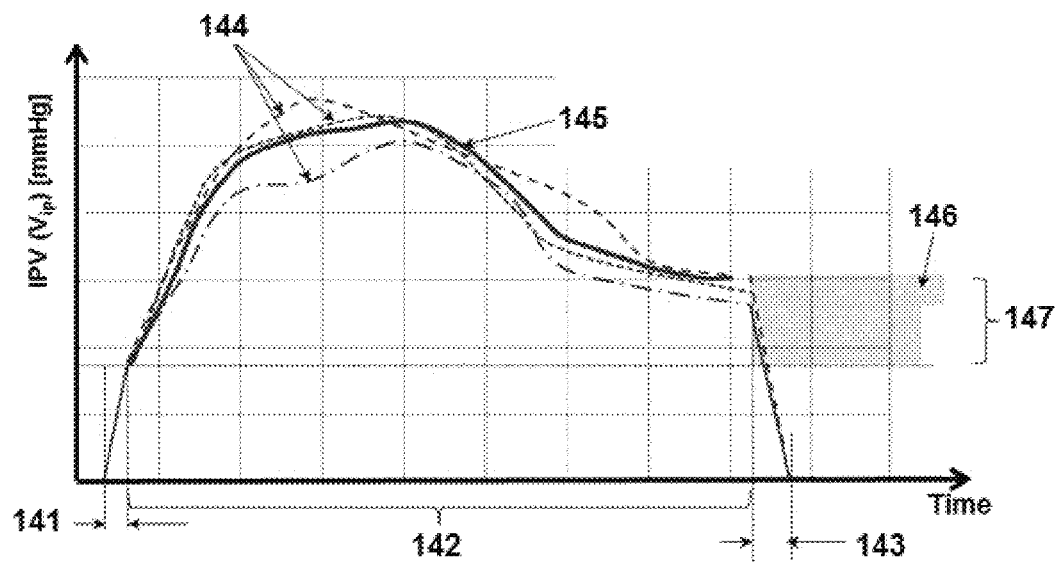
Figure 15:
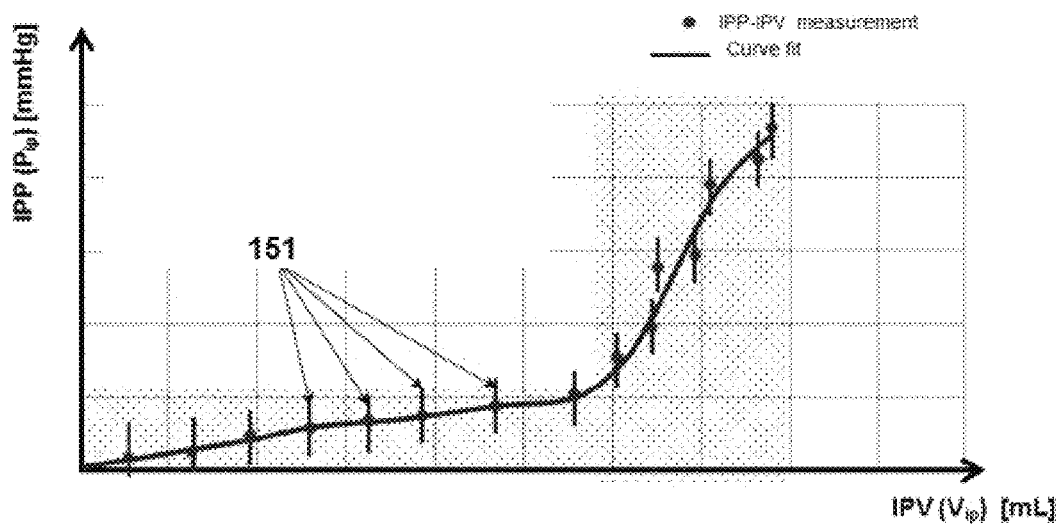
Figure 16:
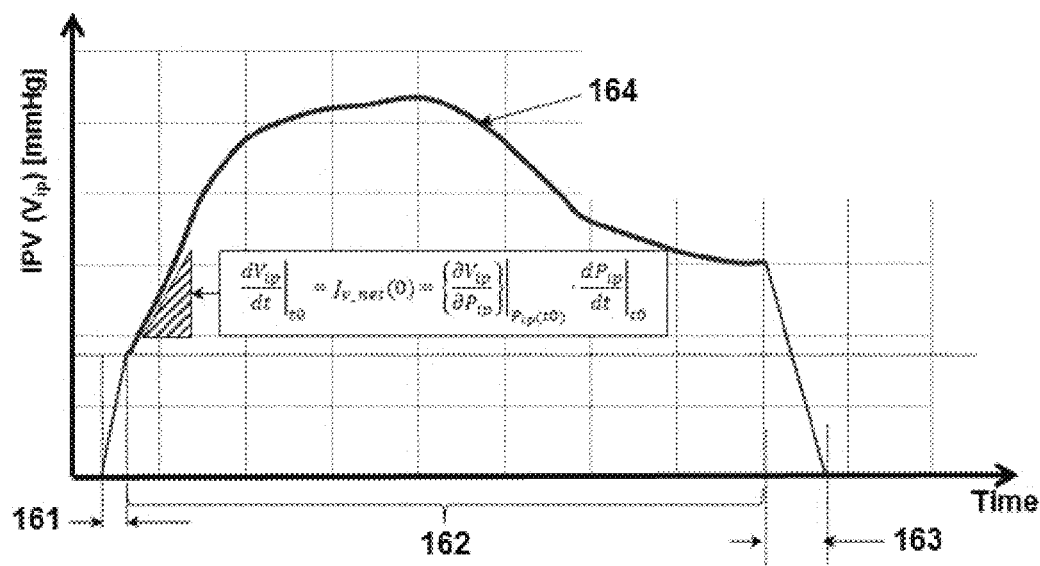
Figure 17:
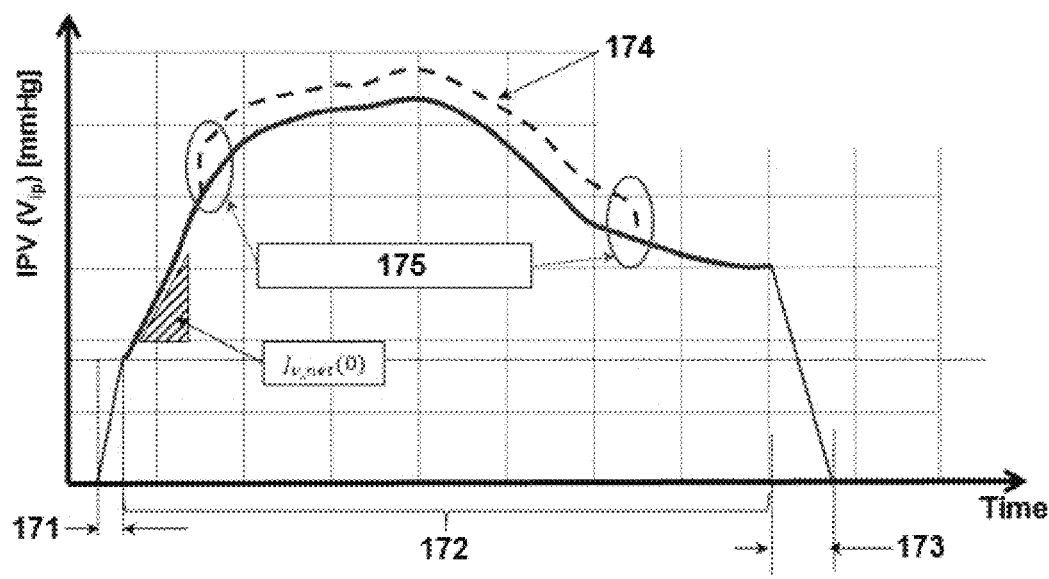
Figure 18:
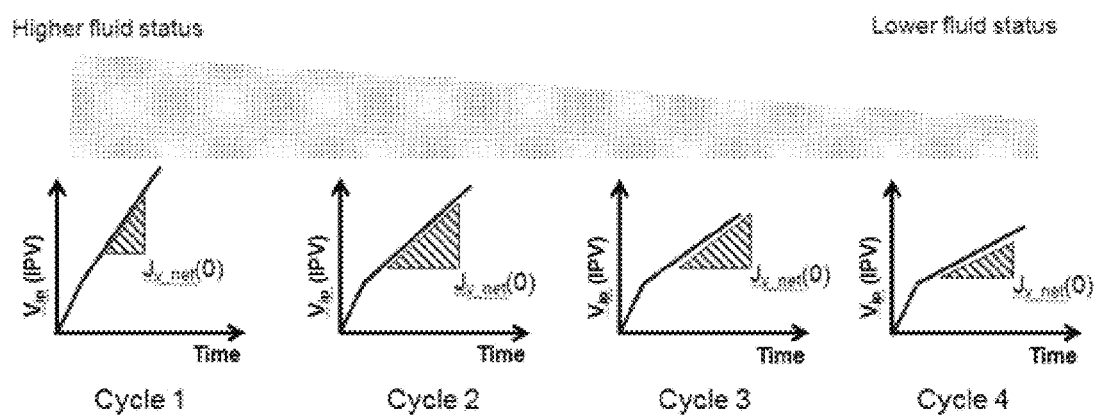
Figure 19:
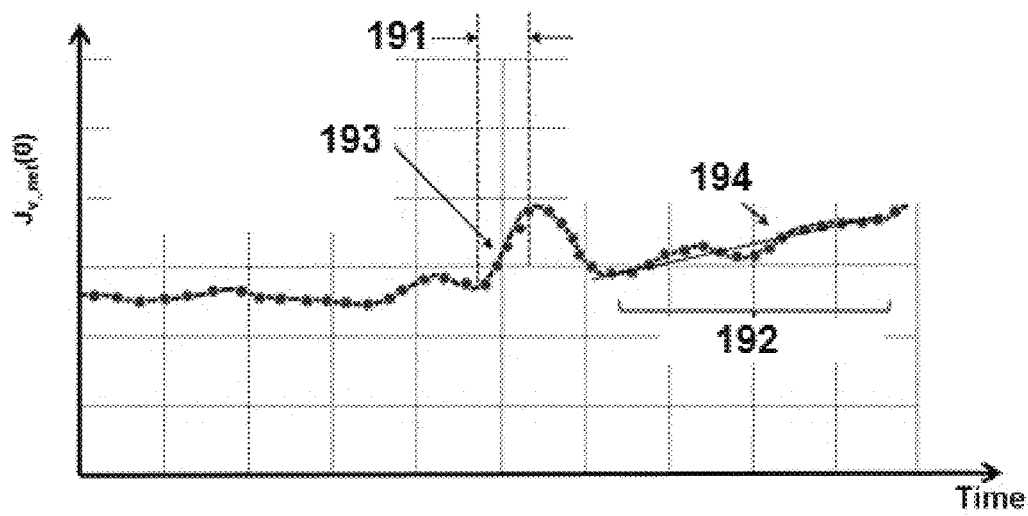
Figure 20:
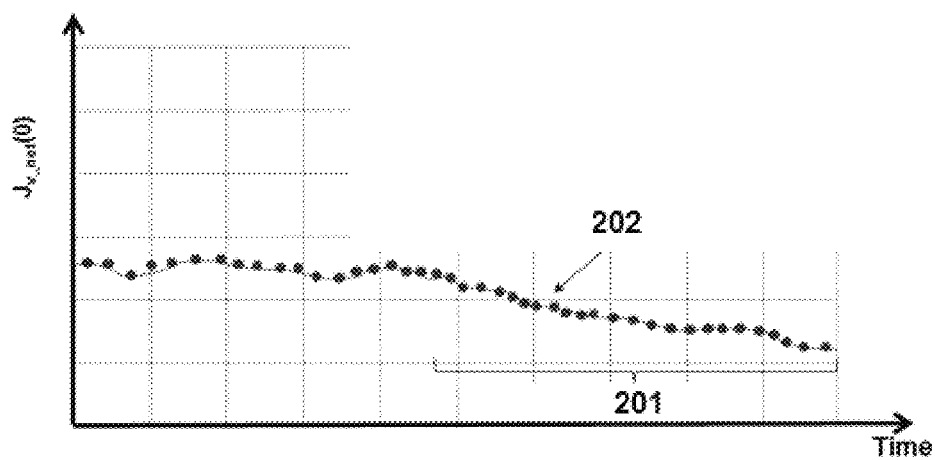
Figure 21:
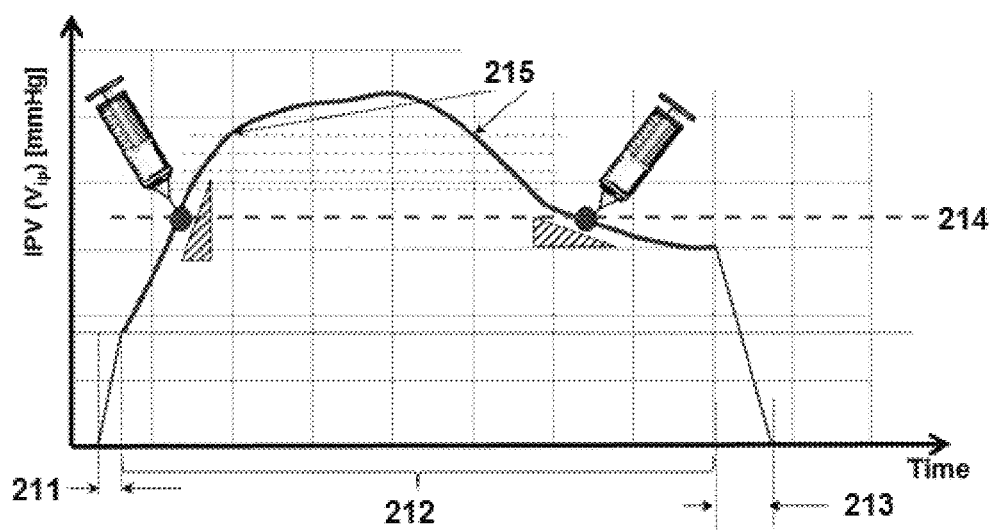

Further details and advantages of the invention are described with reference to the working example. The figures show:

FIG. 1: a relationship of filling volume versus time during a common dialysis treatment;

FIG. 2: a magnified section of the relationship;

FIG. 3: the section of FIG. 2 in conjunction with a corresponding function of intraperitoneal pressure by added volume;

FIG. 4: a schematic representation of IPP measurement;

FIG. 5: an illustration of the location of the relevant pressures when considering the relationship between the IPP ($P_{ip}$) and a pressure sensor located in the controlled flow system;

FIG. 6: stop flow, continuous slow flow and slow down flow profiles;

FIG. 7: hybrid and continuous full speed flow profiles;

FIG. 8: an illustration showing the conditions on either side of a flow transition boundary;

FIG. 9: a schematic illustration of a single load cell gravimetric cycler including relevant hydrostatic pressure heads and flow resistances;

FIG. 10: an illustration of the momentary switching of drain and fill clamps allowing IPP to be determined at intervals during the dwell period;

FIG. 11: an illustration of the non-linear behaviour of an IPP-IPV characteristic;

FIG. 12: an illustration of an arbitrary pressure-volume characteristic in an individual patient;

FIG. 13: an illustration of a superposition of consecutive IPP-IPV characteristics for a particular phase, and an average characteristic can be determined with a least squares fit;

FIG. 14: a graphical representation of a temporal variation of IPV and average dwell behaviour obtained by superimposition of consecutive cycles;

FIG. 15: an illustration of the small variations in IPP superimposed on the mean value of IPP by respiration;

FIG. 16: an illustration of the determination of the initial rate of change of intraperitoneal volume;

FIG. 17: an illustration of changes in posture resulting in a step change in IPP will lead to an apparent shift in IPV;

FIG. 18: an illustration of a progressive reduction initial rate of change of intraperitoneal volume on each successive cycle as fluid status is reduced;

FIG. 19: an illustration of illustrates changes in initial rate of change of intraperitoneal volume provides information to support diagnosis of a variety of clinical conditions FIG. 20: an illustration of a long term decrease initial rate of change of intraperitoneal volume due to aquaporins or development of Encapsulating Peritoneal Sclerosis (EPS); and FIG. 21: an illustration of an isovolumetric (isobaric IPP) sampling that implies conditions where lymphatic flow is equal.

In the example described herein, the inventive apparatus is based on a common automated peritoneal dialysis machine comprising a pump for delivering dialysis fluid to the peritoneal cavity of a patient and a measurement device for measuring the fluid pressure of the delivered dialysis fluid. The device also comprises a control unit operably connected to the pump and the measurement device.

However, the embodiment applied to a gravimetric cycler as well.

FIG. 1 illustrates a function of filling volume versus time during a common dialysis treatment that can be carried out using this type of machine, and which also forms the basis for the inventive implementation.

The treatment starts at time to with an initial outflow to drain fluid from the peritoneal cavity of a patient. After the used dialysis solution is fully drained, an inflow-dwell-outflow cycle is initiated at time $t_1$. The cycle starts with an inflow phase, where a predetermined amount of fresh dialysis fluid is run to the peritoneal cavity. Once the full amount has been delivered at time $t_2$, the dialysis fluid is maintained inside the peritoneal cavity for a predetermined amount of time ($t_3$ minus $t_2$) during a dwell period, during which solutes are exchanged between blood and dialysis solution through the peritoneal membrane. After the end of the dwell period at time $t_3$, the now used dialysis solution is again drained from the peritoneal cavity of a patient. Another inflow-dwell-outflow cycle is then initiated at time $t_4$, and so forth.

FIG. 2 illustrates a magnified section of the function around time $t_1$. According to the invention, the control unit of the dialysis machine is configured to realize an implementation of measuring and recording fluid pressure as follows.

1. Discontinuous Pressure Measurements:

In a first step, the control unit obtains from the measurement device and saves the initial pressure $p_{ini}$ prior the initial outflow at time to and use this as a reference point, i.e., $p_{ini}=0$. Another pressure value $p_{phase}$ is saved at the end of the initial outflow phase, or in other words before starting the inflow phase of the first cycle, at time $t_1$. This value is negative, because the pressure will be lower than prior the initial outflow. In the given example it is −80 mbar. Because the value of $p_{phase}$ is very low, meaning lower than the boundary value of −50 mbar saved in the control unit, the control unit effects the delivery of a predetermined amount of 100 ml of dialysis fluid to the peritoneal cavity and then measures and saves a corrected value $p_1$. The corrected value, in the working example, is −5 mbar. It is assumed to be very close to the hydrostatic pressure due to the low filling volume. The value of $p_1$ serves as reference point for the intraperitoneal pressure, i.e., it is assumed that at $p_1$ the intraperitoneal pressure is zero, IPP=0. It is used to correct all following pressure measurements for the hydrostatic pressure offset in the sense of $IPP_n = p_n - p_1$.

Once the offset has been determined, the control unit continues the inflow and effects a series of fill-and-measurement steps, each step comprising delivering a predetermined quantity of dialysis fluid to the peritoneal cavity and subsequently measuring and recording a pressure value $p_2$, $p_3$, $p_4$, etc. at idle pump. The predetermined quantity of dialysis fluid is 100 ml and the same for all steps. The intraperitoneal pressure is determined for each step using the routine $IPP_2 = p_2 - p_1$, $IPP_3 = p_3 - p_1$, $IPP_4 = p_4 - p_1$ and so forth. A function of IPP versus filling volume of dialysis fluid in the patient is thus established.

This is illustrated in FIG. 3, where the non-linear and convex nature of the function is shown. The pressure increase per added volume hence grows with the overall filling volume because of the increasing peritoneal membrane counter-pressure.

The shape of the function, i.e., the slope and curvature is characteristic of properties of a patient's peritoneal cavity and membrane. It can be used, in conjunction with predetermined empirical values, to output certain therapy-related recommendations, such as optimum filling volume for dialysis fluid in the peritoneal cavity, the optimum dwell time or the optimum amount of inflow-dwell-outflow cycles, or therapy-related predictions, such as overall therapy time or the ultrafiltration volume.

The IPP or any pressure representative therefore may be measured by a sensor.

FIG. 4 shows an embodiment in which a tube 100 (which might be closed by use of a tube clamp if necessary) is connected with the patient catheter 200 which extends into the patient cavity of with a tube connected therewith.

Reference numeral 300 refers to scale which allows the user to read the level of dialysis fluid in the tube 100 which is preferably vertically oriented. Reference numeral 400 is a bag with compliance or tube with hydrophobic membrane.

P is the patient and A is the APD cycler, i.e. the automatic peritoneal dialysis machine.

As shown in the small picture of FIG. 4, right hand side, the zero level for IPP is defined at the height of the armpit of the patient.

The level of the dialysis fluid in tube 100 corresponds to the IPP. This value is taken twice, one after inspiration and one after expiration by the patient, and the arithmetic mean is the IPP value.

2. Continuous Pressure Measurements:

As explained above, the basis for IPP measurement is envisioned as a process of acquiring pressure measurements when fluid is static. The IPP-IPV (Intra Peritoneal Pressure-Intra Peritoneal Volume) characteristic of the peritoneal cavity can be captured by filling the cavity with volume increments then measuring the hydrostatic pressure with the fluid at rest. The drawback of such approach is that it is time consuming and the resolution of the IPP-IPV characteristic is relatively coarse. More sophisticated approaches involving dynamic pressures allowing faster fill and drain durations are described in the following.

2.1. Systems with Controlled (Known) Flow Rate:

Systems with a controlled flow rate relate particularly to pumped cyclers. FIG. 5 depicts the peritoneal membrane, a pressure sensor located remotely in the system providing controlled flow and the relevant pressures are annotated.

Applying the Bernoulli relationship to the variables shown in FIG. 5 leads to $$P_{sen} + \tfrac{1}{2}\rho v_{sen}^2 + \rho g h_{sen} = P_{ip} + \tfrac{1}{2}\rho v_{cath}^2 + \rho g h_2 + \Delta P_f(Q) \qquad \text{Equation 1}$$

where $P_{sen}$ is the pressure at the measurement sensor; $V_{sen}$ is the fluid velocity at the sensor; $V_{cath}$ is the fluid velocity at the catheter tip; $P_{ip}$ is the intraperitoneal pressure which is the sum of the hydrostatic pressure of the peritoneal dialysis fluid instilled and the recoil of the peritoneal cavity walls; $P_f(Q)$ is the pressure drop caused by viscous friction of fluid in motion between the measurement sensor and the catheter tip, dependent on flow rate; $\rho$ is the density of the peritoneal dialysis fluid; g is the gravity constant; $h_2$ is the height difference between the measurement sensor and the catheter tip; and $h_{sen}$ is the height of the measurement sensor relative to the reference point, in this case zero.

In FIG. 5, the peritoneal cavity 51 and the tip 52a of the catheter 52 can be recognized. Spring 53 illustrates the elastic recoil of the peritoneal cavity walls. The catheter tip comprises a sensor 54 to measure $P_{ip}$. The controlled flow system 55 comprises a sensor to measure $P_{sen}$. The reference pressure 56 is illustrated by the base line arrow.

As the pressure sensor is considered to be located at the reference pressure point, Equation 1 reduces to:

$$P_{sen}+\tfrac{1}{2}\rho v_{sen}^2 = P_{ip}+\tfrac{1}{2}\rho v_{cath}^2+\rho g h_2+\Delta P_f(Q) \qquad \text{Equation 2}$$

Under zero flow conditions then $$P_{sens}=P_{ip}+\rho g h_2 \qquad \text{Equation 3}$$

At the end of the initial outflow and $1^{st}$ inflow, the peritoneal cavity is in the empty state with the exception of a small residual volume not accessible by the catheter. In this state, under conditions of zero flow, the IPP ($P_{ip}$) is considered to be zero and the measurement sensor registers the hydrostatic pressure difference between the sensor and the catheter tip which is the term $\mu g h_2$ in Equation 3.

Rearranging for the IPP, $P_{ip}$ then $$P_{ip}=P_{sen}+\tfrac{1}{2}\rho(v_{sen}^2-v_{cath}^2)-\rho g h_2-\Delta P_f(Q) \qquad \text{Equation 4}$$

At the typical volume flow rates during the fill and drain phase in the range of 100-300 mL/min, and the small changes in cross sectional area of the line set and catheter the difference in kinetic energy density (pressure) will be negligible. Therefore Equation 4 may be further reduced to:

$$P_{ip}=P_{sen}-\rho g h_2-\Delta P_f(Q) \qquad \text{Equation 5}$$

2.2. Viscous Friction:

If a dialysis fluid passes through a tube of 0.5 cm diameter at a volume rate of 300 mL/min, the velocity will be approx. 0.25 m/sec. This leads to a Reynolds number of 1250 which satisfies the conditions for laminar flow. Consequently, as dialysis fluid is transported with circular bore tubing, the pressure drop over a section of tubing of length L and radius r for a given flow rate Q may be described by Hagen-Poiseuille's law:

$$\Delta P_f(Q) = \frac{8\mu L Q}{\pi r^4} = R_f Q \qquad \text{Equation 6}$$

$R_f$ represents the hydraulic resistance to flow and will be normally constant for the length of tubing between the catheter tip and the and the pressure sensor. However as $R_f$ is very sensitive to small changes in tube radius will increase the viscous friction $R_f$ and the resultant pressure drop. This can be used to good effect for daily monitoring of the catheter as any accumulation of biofilm in the catheter lumen will cause $R_f$ to increase.

2.2.1. Flow Profiles:

Several different flow profiles may be applied during the fill and drain phases enabling static and dynamic pressure effects to be quantified.

Figure 6A:
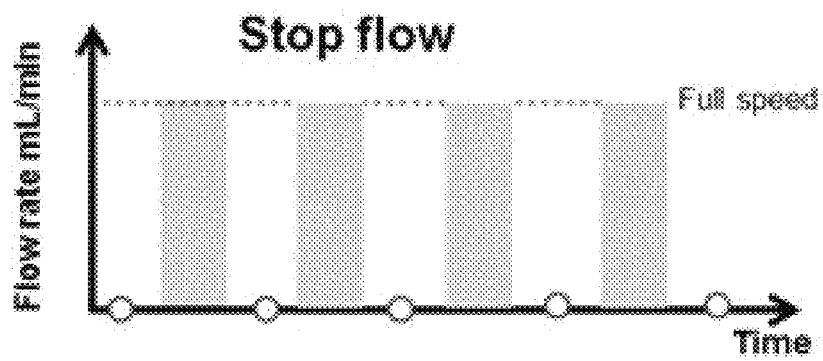

The "Stop Flow" of FIG. 6a. The advantage is that no dynamic pressure effects are observed when the IPP is measured at zero flow conditions. However, the fill and the drain are time consuming when this type of measurement is applied.

Figure 6B:
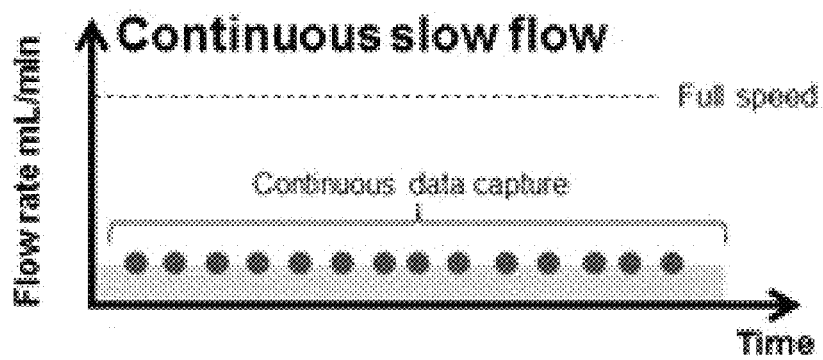

The "Continuous Slow Flow" of FIG. 6b. Advantages of this type of measurement comprise a high resolution in the capture of the IPP-IPV characteristic. Further, the flow rate is sufficiently reduced to minimize dynamic pressure effects. Again, however, the fill and the drain remain time consuming.

Figure 6C:
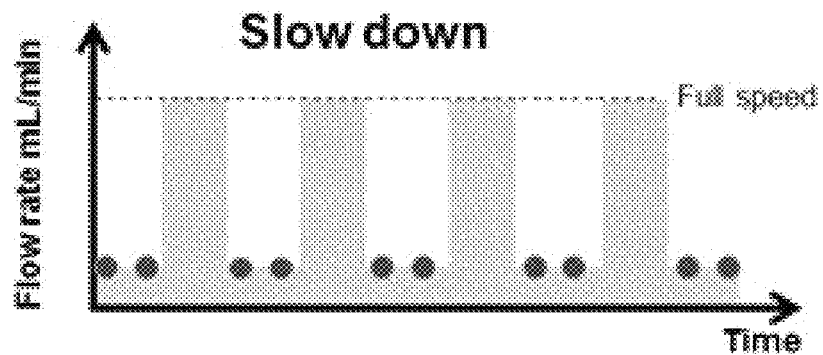

The "Slow Down" of FIG. 6c. Here, the flow rate is slowed down intermittently for data capture such than dynamic pressure effects are minimized. There is an intermittent high resolution when capturing the IPP-IPV characteristic. More data can be obtained by interleaving on the next cycle. Relevant equations can be solved with two different flow rates at the transition boundaries allowing a correction of dynamic pressure effects. The fill and drain phases, however, are still longer.

Figure 7A:
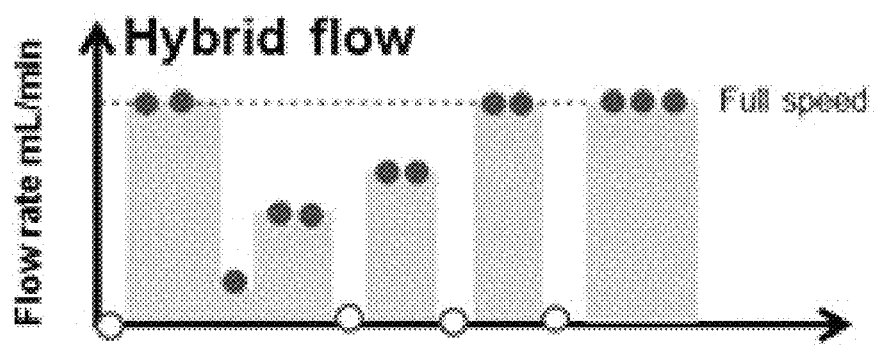

The "Hybrid Flow" of FIG. 7a. Advantages comprise a much greater scope for dynamic pressure generation. This type of measurement also allows for compensation of any non-laminar/disturbed flow, e.g., consideration that the viscous friction is not linear with the flow rate. It causes very little compromise in fill and drain times.

Figure 7B:
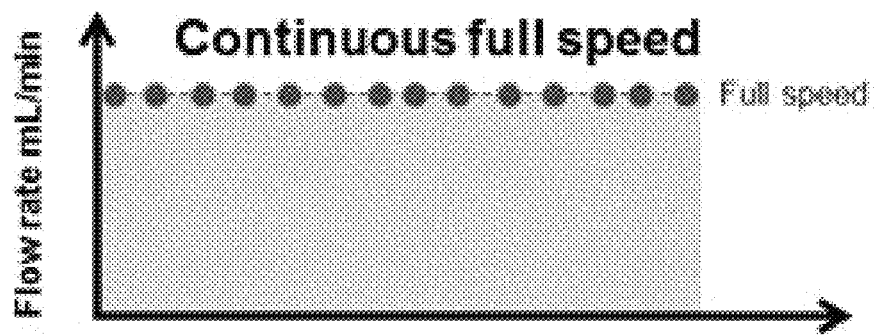

The "Continuous Full Speed" of FIG. 7b. Here, fill and drain times are not reduced at all. However, it requires accurate calculations to compensate for dynamic pressure effects. Characteristics of line set and catheter need therefore be known in advance.

Compensation for the pressure drop caused by viscous friction described by the term $R_fQ$ could be achieved by careful calculation of $R_f$ from tube geometry and application of Equation 6. A more reliable alternative is to determine $R_f$ in situ. This may be achieved by comparing conditions either side of a flow transition boundary as shown in FIG. 8, illustrating the conditions on either side of a flow transition boundary.

Combining Equations 5 and 6 yields $$P_{ip}=P_{sen}-\rho g h_2-R_f Q \qquad \text{Equation 7}$$

If Eq. 7 is applied either side of the flow transition boundary at time T, then $$P_{ip}(T^-)=P_{sen}(T^-)-\rho g h_2-R_f Q(T^-) \qquad \text{Equation 8}$$

and $$P_{ip}(T^+)=P_{sen}(T^+)-\rho g h_2-R_f Q(T^+) \qquad \text{Equation 9}$$

At the flow transition boundary there is no change in IPP, ($P_{ip}$). Therefore Equations 8 and 9 may be equated and solved for $R_f$ which yields $$R_f = \frac{P_{sen}(T^-) - P_{sen}(T^+)}{Q(T^+) - Q(T^+)} \qquad \text{Equation 10}$$

Equation 10 may be applied at any time during the fill and drain phase whenever there is a change in flow, $\Delta Q$, regardless of the sign of the flow transition. Providing the pressure drop is linear with flow then Equation 10 will return the same result for $R_f$. If small non-linear effects come into play then Equation 10 offers the means to apply suitable compensation to the system for IPP measurement defined by Equation 5. Generally larger magnitude flow transitions, $\Delta Q$ will improve the accuracy of $R_f$ but the procedure may be repeated at smaller values of $\Delta Q$ and $R_f$ results averaged.

2.3. Systems with Constant Driving Pressure:

Systems with constant driving pressure apply particularly to gravity based approaches such as CAPD or gravimetric APD cyclers. In CAPD there is no pressure or flow monitoring without dedicated additional hardware. In the case of a gravimetric APD cycler, a load cell allows the flow rate of dialysis fluid and dialysis effluent to be measured. See FIG. 9, that shows a schematic illustration of a single load cell gravimetric cycler including relevant hydrostatic pressure heads and flow resistances.

In FIG. 9, the peritoneal cavity 91 and the tip 92a of the catheter 92 can be recognized. Spring 93 illustrates the elastic recoil of the peritoneal cavity walls. Load cell 95 comprises bags 95-1, 95-2, . . . up to last bag 95-9 that are illustrated in the top of the figure, where the contact is formed by contact area A. A drain bag 96 is illustrated at the bottom of the figure. The catheter lines comprise clamps 97-1 and 97-2 for filling and 98 for draining, Measurement points are labelled A-H.

Determination of IPP via a gravity system without a pressure measurement relies on calculations of dynamic pressures and accurate values of the flow resistance of sections of tubing, as explained in the following. The relevant variables and constants are defined as follows.

Variables: $hf_b$=height of first bags above catheter tip; $h_{lb}$=height of last bag above catheter tip; $h_{PDF}$=height of peritoneal dialysis fluid above catheter tip; $P_{ip}$=Intraperitoneal pressure (IPP); $P_{recoil}$=pressure resulting from elastic recoil of peritoneal cavity; $\Delta m_{cell}$=Change in mass as measured by the load cell during a fill or drain phase; $V_{lb}$=volume of the last bag; $Q_f$=flow rate during a fill/drain phase.

Constants: $A_c$=contact area of filling bags; g=gravity; $\rho$=density of PD fluid.

2.3.1 Calculation of IPP from Inflow of Dialysis Fluid:

The flow rate during fill or drain can be obtained from the rate of mass as measured by the load cell i.e.

$$Q = \frac{1}{\rho} \dot{m}_{cell} \quad \text{Equation 11}$$

During the filling phase when Clamp 97-1 is open (Clamp 97-2 and drain clamp closed), there is a change in height of the first bags, $h_{fb}$ due to the emptying of the first bags (bags 95-1 and 95-2 as indicated in FIG. 9). The change in the height of the first bags $\Delta h_{fb}$ at an arbitrary point in time t is $$\Delta h_{fb}(T) = \frac{\Delta M_{cell}(t)}{A_c \rho} \quad \text{Equation 12}$$

where $\Delta m_{cell}(t)$ is the difference in mass between the initial mass measured by the load cell, $m_{cell}(0)$ and the mass at time t, $m_{cell}(t)$. The pressure head in the first bags is raised due to the pressure exerted by the mass of the last bag above. Therefore the dynamic pressure can be expressed as follows:

$$g\left(\rho h_{fb}(0) - \frac{\Delta M_{cell}(t)}{A_c} + \frac{V_{lb}\rho + M_{lb\_emp}}{A_c}\right) - P_{ip}(t) = Q_f(t)R_{f1} \quad \text{Equation 13}$$

Note that the difference in kinetic energy density can be neglected as argued above. When T=0, i.e. when filling commences at the beginning of treatment, the initial dynamic pressure is $$g\left(\rho h_{fb}(0) + \frac{V_{lb}\rho + M_{lb}}{A_c}\right) - P_{ip}(0) = Q_f(0)R_{f1} \quad \text{Equation 14}$$

Where the overall flow resistance $R_{f1}$ through the relevant sections of tubing is given by $$R_{f1} = (R_{f\_BD}||R_{f\_CD}) + R_{f\_DE} + R_{f\_EG} + R_{f\_FG} \quad \text{Equation 15}$$

Subtracting Equation 13 from Equation 14 yields $$\frac{\Delta M_{cell}(t)}{A_c} + P_{ip}(t) - P_{ip}(0) = (Q_{f1}(0) - Q_{f1}(t))R_{f1}$$

and, by rearrangement $$P_{ip}(t) - P_{ip}(0) = (Q_{f1}(0) - Q_{f2}(t))R_{f1} - \frac{\Delta M_{cell}(t)}{A_c} \quad \text{Equation 16}$$

If the peritoneal cavity is empty then the initial intraperitoneal pressure $P_{ip}$ is zero, then Equation 16 simplifies further to $$P_{ip}(t) = (Q_{f1}(0) - Q_{f2}(t))R_{f1} - \frac{\Delta M_{cell}(t)}{A_c} \quad \text{Equation 17}$$

It is clear from Equation 17 that IPP is obtained entirely from load cell measurements and knowledge of the flow resistance and bag contact area. Equation 17 is valid providing that IPP is assumed constant for a short period of time during which the value of flow rate is observed. The height of the catheter tip relative to the first bags, $h_{fb}$ (0) and the pressure exerted by the last bag are not required as these cancel out in the working although. However this in only valid provided that $h_{fb}$ (0) remains constant which implies that the position of the patient in height relative to the dialysis fluid bags is unchanged.

2.3.2. Calculation of IPP from Outflow:

During outflow there is an additional restriction in that the height of the patient (the catheter tip) above the drain bags must be supplied as the initial conditions of the IPP immediately prior to drain are unknown. To be clear, this restriction does not arise in the filling phase provided that IPP=0 is assumed as the reference immediately prior to the initial inflow.

When the drain clamp in opened, then following similar principles as described above, the relevant expression for the dynamic pressure drop on the drain side is:

$$g\left(\rho h_{pat}(0) - \frac{\Delta M_{cell}(t)}{A_c}\right) + P_{ip}(t) = Q_d(t)R_d \quad \text{Equation 18}$$

The IPP, $P_{ip}(t)$ can be determined from Equation 18, noting that the change in cell mass $\Delta M_{cell}$ is the change relative to the cell mass immediately prior to the start of the drain phase. Given that the flow resistance Rd must be known, calculation of IPP from outflow does not add any additional value compared to IPP determined from inflow measurements.

2.3.3. Measurement of IPP During the Dwell Period:

If the fill and drain clamps are switched in sequence, there exists the opportunity to measure IPP at the switching intervals. The drain clamp is opened momentarily to release an aliquot of dialysis effluent which is followed by a reinfusion of fresh dialysate fluid by opening the fill clamp momentarily. Ideally the volumes of dialysis fluid and dialysis effluent are matched so that there is no change to the current IPV. See FIG. 10, which illustrates the momentary switching of drain and fill clamps allowing IPP to be determined at intervals during the dwell period. In this figure, fill phase 101, dwell phase 102 and drain phase 103 can be recognized. The momentary switching of fill and dran clamps is illustrated by reference numerals 104. During the short interval when the drain clamp is open, Equation 17 can be applied to determine the IPP.

3. Individual Pressure-Volume Characteristic of the Peritoneal Cavity:

During the filling phase when a PD fluid is introduced into the peritoneal cavity a hydrostatic pressure is developed. Although attempts have been made to quantify the relationship between intraperitoneal volume and intraperitoneal pressure, there is considerable inter-patient and intra-patient variation. The elasticity of the membrane cannot be predicted and furthermore due to the highly convoluted anatomy of the peritoneal cavity may lead to discontinuities and non-linearity of the pressure-volume characteristic.

In order to derive information about the peritoneal membrane particularly the dwell behaviour, arguably the best approach is to identify the pressure-volume characteristic by measurement in the individual patient. This may be achieved via a suitable method (as described earlier in the initial IPP submission) and may lead to a characteristic such as that shown in FIG. 11, which illustrates the non-linear behaviour of an IPP-IPV characteristic. In the figure, reference numeral 111 designates the peritoneal cavity. The convoluted folded structure of the peritoneal membrane as shown leads to cavity manifested as pockets of fluid. Reference numeral 112 illustrates the hydrostatic pressure developed as the cavity is filled. Reference numeral 113 illustrates the unstressed volume of the peritoneal cavity. Reference numeral 114 illustrates the recoil/elastic change of the peritoneal cavity, i.e., the stressed volume. A primary non-linearity 115 arises from the stressed-unstressed volume interface. At this point, PD fluid is in full contact with the surface area of the membrane. Secondary non-linearities 116 arise from the convoluted anatomy of the peritoneal cavity. Further non-linearities 117 arise from the convoluted anatomy of the peritoneal cavity beyond point 115.

Two sources of non-linearity in the IPP-IPV characteristic may be identified. Depending on the patient, a primary non-linearity may arise at the stressed to unstressed volume transition (S-U transition). The S-U transition reflects a change in the gradient between the conditions of unstressed and stressed volume. At the S-U transition, the peritoneal cavity is fully filled and the instilled PD fluid is in full contact with the available membrane area. Further increases in volume beyond the S-U transition point of primary leads to elastic pressure exerted on the peritoneal volume.

There is no guarantee that the S-U transition will be encountered in a given patient, i.e. the pressure behaviour in stressed and unstressed volume states may be similar and the S-U transition cannot be resolved. If the membrane has been subject to fibrosis and this leads to reduced elasticity of the membrane the S-U transition may be more apparent.

The S-U transition provides a possible criterion for setting a patient's individual fill volume, although this may be completely different to the maximum fill volume tolerated by the patient. In any case the IPP will increase further beyond the S-U point due to ultrafiltration during the swell phase.

Secondary non-linear behaviour can be expected in any patient due to the highly convoluted and folded anatomical structure of the peritoneal membrane. During the filling phase pockets of the peritoneal cavity become accessible sequestering fluid without necessarily contributing to a change in IPP.

Ideally the IPP-IPV characteristic should be measured up to the maximum IPP tolerated by the patient (max fill volume) as indicated in as this allows full use of the IPP-IPV characteristic in fill, dwell and drain phases. Once IPP measurement data has been acquired, the IPP-IPV characteristic can be represented either with a suitable polynomial or a set of piecewise linear approximations.

Beyond the maximum IPP measured when determining the pressure-volume characteristic the gradient is assumed to be linear. Allowances must be made for factors that lead to intra-patient variation of the pressure-volume characteristic in the short term such as changes in body posture, movement of the catheter-tip, bowel obstruction etc. A different body posture may introduce an offset on the IPP axis, while variations in residual volume caused by incomplete drainage will lead to a shift of the IPV origin when identifying the pressure-volume characteristic. See FIG. 12, which illustrates an arbitrary pressure-volume characteristic in an individual patient.

In the Figure, the $IPV_{origin}$ 121 at the start of the cycle may be subject to variation as incomplete drain from the peritoneal cavity results in variations in residual volume. Likewise, a different posture may introduce an offset in the IPP axis 122. The filling phase or drain phase is designated by reference numeral 123, the filling volume (prescription) by reference numeral 124. The IPP-IPV characteristic during an initial fill phase is illustrated by reference numeral 125. The IPP-IPV characteristic during a drain phase is illustrated by reference numeral 126. The relevant operating range during the dwell is illustrated by reference numeral 127. An arbitrary limit of IPP-IPV characteristic determined by measurement, i.e., the maximum fill volume is designated by reference numeral 128. Reference numeral 129 designates a linear relationship that can be assumed beyond the maximum IPP measured when determining the IPP-IPV characteristic.

Once a set of pressure-volume characteristics have been obtained and cross correlated, shift of the IPV origin will identify changes in residual peritoneal volume.

Given that the peritoneal membrane has complex elastic behaviour, further allowance must be made for a hysteresis loop over the fill-drain cycle. In a particular direction such as the fill phase, the pressure volume characteristic can be captured over consecutive cycles and superimposed as indicated in FIG. 13, which illustrates a superposition of consecutive IPP-IPV characteristics for a particular phase, and an average characteristic can be determined with a least squares fit. Specifically, the pressure-volume characteristics from consecutive cycles are illustrated by reference numeral 131 and the average characteristic obtained by superposition is illustrated by reference numeral 132. Furthermore during each cycle, IPV-IPP data pairs can be obtained at different IPV interval thus increasing resolution over a treatment.

The same procedure may be applied to the drain phase providing an IPP-IPV characteristic for the drain phase. If a drain alarm occurs during subsequent routine treatments, the IPP-IPV characteristic can be used as a reference to help diagnose the cause of the drain alarm.

In FIG. 13 the IPP is considered as the dependent variable, i.e. the pressure that is developed for a given (known) IPV. During the dwell period the IPV changes due to ultrafiltration cannot be measured directly. However, with prior knowledge of the pressure-volume characteristic, the IPV can be estimated by inverting the pressure-volume characteristic such that IPV becomes the dependent variable of the measured IPP. Through this approach IPV may be estimated for any measured value of IPP during the dwell phase and thus the dwell behaviour may be obtained in terms of the temporal variation of IPV. A graphical representation of a temporal variation of IPV and average dwell behaviour obtained by superimposition of consecutive cycles is illustrated in FIG. 14.

Specifically, the fill phase 141, dwell phase 142 and drain phase 143 are marked on the x-axis of the graph. Reference numeral 144 designate the temporal variations of IPV for consecutive cycles. Reference numeral 145 designates the average dwell behavior derived from consecutive cycles. The UFV is designated with reference numeral 147, with variation in UFV between consecutive cycles illustrated by 146. The graph applies only under the condition that there is no change to the prescription over the number of consecutive cycles.

Providing the prescription remains unchanged (patient is treated with the same glucose composition and filling volume) the average IPV behaviour may be obtained by superposition.

3.1. Respiration:

During respiration, pressure on the diaphragm is transmitted to the peritoneal cavity. Expiration leads to a fall in IPP while inspiration causes IPP to rise. The variation in IPP due to respiration, $\delta P_{ip\_Resp}$ is typically of the order of 4 cm $H_2O$, imposed on the mean value as indicated in FIG. 15, which illustrates the small variations in IPP superimposed on the mean value of IPP by respiration. Reference numeral 151 designates the variability in IPP due to respiration, $\delta P_{ip\_Resp}$.

As a consequence of respiration, capture of the mean value of the IPP-IPV characteristic require algorithms to compensate for $\delta_{Pip\_Resp}$ to differentiate respiration from the secondary non-linear effects of cavity wall folding/unfolding. Several compensation options are possible, e.g. measurement of the amplitude of $\delta P_{ip\_Resp}$ when catheter flow is stopped for a short period of time and determination of the respiration rate by frequency analysis of the IPP signal.

In any case compensation for respiration during the dwell phase will also be necessary in order to capture the dwell behaviour. Nevertheless, the variation $\delta P_{ip\_Resp}$ due to respiration may be processed further as it is likely that $\delta P_{ip\_Resp}$ may be modified in amplitude and frequency by the mean IPP and state of consciousness. 0

3.2. Affecting UFV by Drain Optimization:

By superposition of IPP data over successive cycles and its transformation to IPV (through the IPP-IPV characteristic), the average dwell behaviour can be obtained without the need to employ any sophisticated model of fluid transport into the peritoneal cavity. These data can be acquired automatically for every cycle and every treatment without any user intervention or significant impact on treatment time. Over a period of weeks and months subtle changes in the mechanical properties of the peritoneal cavity can be tracked.

Once the average dwell behaviour has been captured, the options for influencing the ultrafiltration now become more apparent by simply optimising the drain through shorter or longer dwell durations. This has the advantage that some degree of ultrafiltration control is possible without the need to change glucose composition. This approach is only valid provided the prescription remains unchanged. Nevertheless, if the prescription is revised with a new fill volume or glucose composition for example, the above process may be repeated to obtain an update of the average dwell behaviour.

4. Initial Rate of Rise of IPV:

Once a PD fluid has been instilled, the initial rate of change of IPV provides valuable information about fluid transfer across the peritoneal membrane. The local gradient of the pressure-volume characteristic evaluated for a given value of IPP, ($P_{ip}$) provides the basis for estimating the rate of change of IPV, ($V_{ip}$) derived from IPP measurements. This may be expressed as $$\left.\frac{dV_{ip}}{dt}\right|_{t0} = J_{v_{net}}(0) = \left\{\frac{\partial V_{ip}}{\partial P_{ip}}\right\}\bigg|_{P_{ip}(t0)} \cdot \left.\frac{dP_{ip}}{dt}\right|_{t0} \quad \text{Equation 19}$$

where
$V_{ip}$=IPV,
$P_{ip}$=IPP, t0 is the time at the start of the dwell, immediately following the instillation of PD fluid;

$$\left\{\frac{\partial V_{ip}}{\partial P_{ip}}\right\}\bigg|_{P_{ip}(t0)}$$

is the local gradient of intraperitoneal volume with respect to pressure evaluated at the pressure observed when t=0. This is derived from the IPP-IPV characteristic;

$$\left.\frac{dP_{ip}}{dt}\right|_{t0}$$

is the initial rate of change of intraperitoneal pressure derived from IPP measurements during the initial interval ($\Delta t$) of the dwell. This could be either a linear fit of IPP measurements over the interval $\Delta t$ or a simple 1st order fit if the rate of change of IPP decreases more rapidly over the interval $\Delta t$;

$$\left.\frac{dV_{ip}}{dt}\right|_{t0}$$

is the calculated initial rate of change of intraperitoneal volume, which may be rewritten as $J_{v\_net}(0)$; and $J_{v\_net}(0)$ represents the most rapid change in IPV under condition where the crystalloid osmotic gradient is highest as depicted in FIG. 16, which illustrates this determination of the initial rate of rise of IPV, $J_{v\_net}(0)$.

In FIG. 16, the fill phase 161, dwell phase 162 and drain phase 163 are marked on the x-axis of the graph. Reference numeral 164 designates the curve representative for the average dwell behavior derived from consecutive cycles.

The magnitude of $J_{v\_net}(0)$ is dependent on factors such as osmotic gradients across the membrane and hydraulic conductance of the membrane. Hydraulic conductance reflects a number of anatomical changes in the peritoneal membrane such as pore density, the type of pores, membrane surface area and capillary recruitment. Under the conditions where there is no change to the prescription over an observation period of interest, then $J_{v\_net}(0)$ monitored over successive treatments provides valuable diagnostic insight into a range of clinically important issues. These clinical applications are outlined in the following sub sections. It is expected that the prescription will change from time to time if and this relates to a change in glucose concentration particular, this will influence $J_{v\_net}(0)$. Similarly even within a single treatment some PD systems allow cycles to be performed with different glucose composition.

Changes to glucose composition do not detract from the clinical applications. The relevant condition that need to be applied is that $J_{v\_net}(0)$ from different cycles and treatment is compared with the same glucose composition so that the effect of osmotic gradients can be eliminated allowing other influences on $J_{v\_net}(0)$ to be exposed. $J_{v\_net}(0)$ can be acquired in the time frame of a few minutes during which the patient should limit movements. If the local gradient $$\left\{ \frac{\partial V_{ip}}{\partial P_{ip}} \right\} \bigg|_{P_{ip}(t0)}$$

is relatively constant at the IPP (Pip) at which $J_{v\_net}(0)$ will be relatively insensitive to changes in posture.

4.1 IPV Artefact Rejection:

Patient movement, especially changes in posture causes instantaneous changes in IPP. The magnitude of the IPP depends on the location of the catheter tip relative to the system of IPP measurement and the hydrostatic pressure head of fluid above the catheter tip in the peritoneal cavity. While the IPP can change instantaneously, the IPV by contrast changes only due to the net volume flow into the peritoneal cavity.

The IPV is calculated through knowledge of the IPP-IPV characteristic and the measured IPP. This means that any step changes in IPP are translated directly to the IPV leading to a measurement artefact as illustrated in FIG. 17, which shows changes in posture resulting in a step change in IPP will lead to an apparent shift in IPV.

In FIG. 17, the fill phase 171, dwell phase 172 and drain phase 173 are marked on the x-axis of the graph. Reference numeral 174 designates a measurement artifact, i.e., an apparent shift in IPV due to a change in posture 175.

Fluid transport models of the peritoneal cavity and peritoneal membrane can be applied to obtain membrane parameters. Thus the temporal variation in IPV as measured is an especially valuable input for parameter determination. Once the behaviour of either a single dwell or a series of dwells can be captures in the model, it is then possible to predict the behaviour of different prescriptions and treatment regimens. In in order to derive such value in practical application, model need to be robust to IPV artefacts.

During the dwell phase the rate of variation of IPV is unlikely to exceed the value of $J_{v\_net}(0)$. Additionally the ΔIPP due to a posture change (recumbent to standing) is known from the procedure used to identify catheter migration as described earlier. These criteria may be built into algorithms for IPV artefact rejection.

4.2 Fluid Status Tracking Over Consecutive Cycles:

The fluid status of a patient influences both capillary pressure and capillary recruitment. The vascular beds which surround the peritoneal cavity form part of the anatomical structure of the peritoneal membrane. A decrease in the degree of capillary recruitment due to a reduction of fluid status can lead to a decrease in the average hydraulic conductance of the peritoneal membrane. Furthermore under conditions of reduced fluid status, capillary pressure may be decrease additionally. If either the pressure gradient across the peritoneal membrane is reduced or the hydraulic conductance reduced, the volume flow, $J_{v\_net}$ will decrease.

During overnight cycling in particular, a patient's fluid intake is likely to be very limited or even nil. Therefore with each successive cycle resulting in net ultrafiltration, the fluid status will be reduced. If the patient's fluid status is influenced sufficiently to cause modification of capillary recruitment or capillary pressure this will be reflected in a progressive reduction in volume flow $J_{v\_net}(0)$ as indicated in FIG. 18, which illustrates a progressive reduction in $J_{v\_net}(0)$ on each successive cycle as fluid status is reduced. If there is no change to $J_{v\_net}(0)$ over successive cycles, this may be indicative of more severe fluid overload.

This approach is valid providing there is constancy in the prescription between consecutive cycles (same fill volume and same glucose content) and the peritoneal cavity undergoes a complete drain at the end of each cycle.

Applied in isolation, this approach is especially suited to fluid status tracking. When used in conjunction with a measurement of fluid status or an assessment of residual renal volume further diagnostic capability is afforded. One particular advantage is that the magnitude of $J_{v\_net}(0)$ provides a measure of the intravascular fluid status which may be distinguished from extracellular fluid status.

Mathematical models of peritoneal transport kinetics that have been developed to date typically consider only a single cycle. Modelling over several successive cycles, especially with $J_{v\_net}(0)$ as input data provides the opportunity to extend the capability of models for the purposes of UF prediction. Application of model based methods may also offer the opportunity to track changes in fluid status but in the context of incomplete drains or tidal prescriptions.

4.3 Increases in $J_{v\_net}(0)$:

A transient rise in $J_{v\_net}(0)$ over a period of days could be indicative of an acute inflammatory response of the peritoneal membrane caused by an episode of peritonitis for example. This results in a leakier membrane (a rise in the hydraulic conductance) particularly with regard to large pore fluid and protein transport. Thus a rapid rise in $J_{v\_net}(0)$ can serve as an early warning of the possible onset of peritonitis. Furthermore, rapid restoration of $J_{v\_net}(0)$ provides feedback that treatment intervention for an episode of peritonitis has been successful. See FIG. 19, which illustrates changes in $J_{v\_net}(0)$ provides information to support diagnosis of a variety of clinical conditions.

As illustrated in FIG. 19, in a timeframe 191 of days a rapid rise 193 in $J_{v\_net}(0)$ can be observed, which could relate to the onset of a peritonitis period. In a timeframe 192 of weeks to months, a long term rise 194 of $J_{v\_net}(0)$ could be observed, which could relate to increasing hydraulic conductance.

Rapid changes in $J_{v\_net}(0)$ may also reflect changes in a patient's fluid status. Angiogenesis of the peritoneal vascular beds is a known phenomenon in PD patients and has the effect of increasing pore area over extended periods of time (weeks to months). This is manifested as a rise in the hydraulic conductance.

Increased fluid status may also influence $J_{v\_net}(0)$. In order to resolve the cause of a rise in $J_{v\_net}(0)$, further investigation can then be justified such as a measurement of fluid status, urine output or analysis of a sample of dialysis effluent for signs of infection. An appropriate membrane test could be performed to investigate factors related to hydraulic conductance.

4.4 Decreases in $J_{v\_net}(0)$:

A decrease in $J_{v\_net}(0)$ may be less common and most likely only an effect that can be observed over a longer period of time (months to years) as depicted in FIG. 20, which shows a long term decrease in $J_{v\_net}(0)$ due to aquaporins or development of EPS. Gradual loss of aquaporin function leads to a fall in the average hydraulic conductance of the peritoneal membrane and hence a reduction in $J_{v\_net}(0)$. Encapsulating Peritoneal Sclerosis (EPS) is a condition which can occur in some PD patients and describes a variety of conditions which change the peritoneal membrane function. These conditions include peritoneal fibrosis, thickening of the membrane for example which all have the effect of reducing hydraulic conductance.

As illustrated in FIG. 20, in a timeframe 201 of months to years a long term decrease 202 in $J_{v\_net}(0)$ can be observed, which could relate to the loss of aquaporins or development of EPS.

When interpreting the long term fall in $J_{v\_net}(0)$, allowances need to be made for changes in fluid status as significant dehydration will lead to a reduction in $J_{v\_net}(0)$ in just the same way urine output is decreased. Once fluid status has been eliminated a fall in $J_{v\_net}(0)$ is unlikely to recover due as long as some anatomical changes of the peritoneal membrane remain irreversible. The long term fall in $J_{v\_net}(0)$ thus provides a useful prognostic tool in predicting time to technique failure attributed to a deterioration of the peritoneal membrane.

5. Determination of Hydraulic Conductance:

A method to determine the osmotic conductance due to glucose is described in the literature Rippe B '*Fluid and electrolyte transport across the peritoneal membrane during CAPD according to the three-pore model*' Perit Dial Int 2004; 24: 10-12 and is the basis of the 'Double Mini-Peritoneal Equilibrium Test' described by La Milia et al. 'Simultaneous measurement of peritoneal glucose and free water osmotic conductances', Kidney International (2007) 72, 643-650. The procedure involves instillation of dialysis fluid with glucose composition of 1.36% and 3.86% in two cycles respectively. In each cycle, the peritoneum is drained after 1 hour and the glucose content of the dialysate is determined. The following method which is aimed at identification of the average hydraulic conductance (UF coefficient) of the peritoneal membrane represents a similar approach, but the crucial differences are that it: avoids the need for two cycles PD fluid of with two PD fluid instillations of specific glucose content; avoids the need to drain the dialysis fluid after one hour; avoids the need for a correction factor to be applied to account for glucose dilution effects due to any residual volume in the peritoneum; requires measurements of IPP during the dwell a glucose in a dialysate sample during the dwell; and requires only a single cycle.

The variation in intraperitoneal volume given by Equation 20, is described in Rippe B, Stelin G Haraldson B. '*Computer simulations of peritoneal fluid transport in CAPD*', Kidney Int 1991; 40: 315-325

$$\frac{dV_{ip}}{dt} = J_{v\_net} = L_p S\left(\Delta P - \sigma_{prot}\Delta\pi_{prot} - \sigma_g\Delta\pi_g - \sum_i^n \sigma_i\Delta\pi_i\right) - Jv_{Lymph}$$

Equation 20 where $L_p S$ is the total hydraulic conductance or UF coefficient due to the sum of partial hydraulic conductance for each pore pathway; $\Delta$ indicates the differential with respect to the capillary beds surrounding the peritoneal cavity and the intraperitoneal cavity; $\sigma$ represents the average reflection coefficient dependent on the ratio of aquaporin, small and large pores; $\Delta P$ is the average differential hydraulic pressure; $\sigma_g \Delta\pi_g$ is the differential osmotic pressure due to glucose, attenuated by the average reflection coefficient of glucose $\sigma_g$; $\sigma_{prot} \Delta\pi_{prot}$ is the differential oncotic pressure due to protein, attenuated by the average reflection coefficient of protein $\sigma_{prot}$; $\sigma_i \Delta\pi_g$ represents the differential osmotic pressure due to all other osmotically active solutes, attenuated by the average reflection coefficient $\sigma_i$ for the ith solute; $Jv_{Lymph}$ is the volume flow of lymphatic fluid; and $J_{v\_net}$ is the net volume flow rate into the peritoneal cavity.

The differential hydrostatic pressure is the difference between the average capillary pressure Pcap and average intraperitoneal pressure $P_{ip}$ and is expressed as:

$$\Delta P = P_{cap} - P_{ip}$$

Equation 21

Equation 20 may be considered at two different points in time $t_1$ and $t_2$ during a dwell from which a difference expression may be developed. Assuming constancy of capillary side plasma protein, lymphatic flow, and that the contribution of other osmotically active solutes ($\sigma_i \Delta\pi_i$) is negligible, many factors influencing the rate of change of intraperitoneal volume cancel out. Applying these assumptions, Equation 20 may be written as a difference equation for two different points in time, $t_1$ and $t_2$ during a dwell yielding:

$$\left.\frac{dV_{ip}}{dt}\right|_{t_1} - \left.\frac{dV_{ip}}{dt}\right|_{t_2} \approx L_p S[P_{ip}(t_1) - P_{ip}(t_2) + \sigma_g(\Delta\pi_g(t_2) - \Delta\pi_g(t_1))]$$

Equation 22

By Van't Hoff's law $$\Delta\pi_g(t) = RT(C_{g\_cap}(t) - C_{g\_ip}(t))$$

Equation 23

The glucose concentration in the capillary beds, $C_{g\_cap}$ (plasma glucose) is also considered constant in the context of single dwell so Equation 22 reduces further to:

$$J_{v\_net}(t_1) - J_{v\_net}(t_2) \approx L_p S[P_{ip}(t_1) - P_{ip}(t_2) + \sigma_g RT(C_g(t_2) - C_g(t_1))]$$

Equation 24

Substituting the form of Equation 19 and rearranging for the average hydraulic conductance $L_p S$ yields:

$$L_p S \approx \frac{\left\{\frac{\partial V_{ip}}{\partial P_{ip}} \cdot \frac{dP_{ip}}{dt}\right\}\bigg|_{t_1} - \left\{\frac{\partial V_{ip}}{\partial P_{ip}} \cdot \frac{dP_{ip}}{dt}\right\}\bigg|_{t_2}}{[P_{ip}(t_1) - P_{ip}(t_2) + \sigma_g RT(C_g(t_2) - C_g(t_1))]}$$

Equation 25

In order to determine $L_p S$ with accuracy, $t_1$ and $t_2$ should be chosen where differences in the magnitude of the rates of change of IPP ($|dP_{ip}/d_t|$) are large. Improved accuracy may be achieved by considering the conditions at more than two points in time during the dwell.

5.1 Properties at Isovolumetric IPV and Isobaric IPP Conditions:

During the dwell phase, provided that the dwell duration is of sufficient length, there is a characteristic initial rise in IPV followed by a later fall in IPV. This means that there are periods of the dwell where a continuum of two identical values of IPV are encountered which translate to identical values of IPP. Under the assumption that IPP is the principle determinant of the magnitude of lymphatic flow it stands to reason that that there are periods of the dwell giving rise to in a continuum of two identical lymphatic flow rates. See FIG. 21, which illustrates an isovolumetric (isobaric IPP) sampling that implies conditions where lymphatic flow is equal. It is immaterial whether the relationship between lymphatic flow rate and IPP is non-linear.

In FIG. 21, the fill phase 211, dwell phase 212 and drain phase 213 are marked on the x-axis of the graph. Reference numeral 174 designates points of isovolumetric sampling. The curve 215 is illustrative of the continuum of ideal lymphatic flow rates.

The determination of average hydraulic conductance, $L_pS$ by Equation 25 requires two glucose samples of the intraperitoneal fluid. If the timing of these samples is arranged under isobaric IPP conditions then the influence of the lymphatic flow is eliminated completely. This improves the approximation of Equation 22 which means the average hydraulic conductance, $L_pS$ can be determined with greater accuracy.

This is due to the initial oncotic pressure gradient of glucose followed by a later fall in IPP due to the reabsorption of fluid via the lymphatic system and dissipation of the oncotic pressure gradient by absorption of glucose through the small pore.

6. Lymphatic Flow Rate Estimation:

Knowledge of the average hydraulic conductance $L_pS$ allows an estimate of lymphatic flow rate to be obtained provided information is supplied relating to total protein and glucose from both plasma and dialysate side measurements. Thus if capillary pressure is assumed at ca. 25 mmHg and both the IPP, $P_{ip}$ and rate of change of IPV, $J_{v\_net}$ are determined at the time of sampling then the lymphatic flow rate, $J_{vLymph}$ may be obtained by rearrangement of Equation 20, i.e.

$$Jv_{Lymph} \approx L_pS(P_{cap}-P_{ip}-\sigma_{prot}\Delta\pi_{prot}-\sigma_g\Delta\pi_g)-J_{v\_net} \qquad \text{Equation 26}$$

To summarize, it can be stated that the invention uses the IPP measurement to output therapy-related predictions or recommendations and offer means to perform drain optimisation to afford better control of UF, means to track changes in fluid status, greater visibility to peritoneal cavity drainage issues, early warning detection of peritonitis, determination of the average hydraulic conductance (UF coefficient) of the peritoneal membrane (a major factor in the delivered UF), an online frequent tracking of peritoneal membrane function and a tracking of aquaporin loss and EPS progression.

The invention claimed is:

1. An apparatus for performing peritoneal dialysis, the apparatus comprising means for cyclically delivering dialysis fluid or enabling gravity flow of dialysis fluid to the peritoneal cavity of a patient, a measurement device for measuring the fluid pressure of the delivered dialysis fluid or the fluid pressure in the peritoneal cavity, and a control unit operably connected to said means and the measurement device, wherein the control unit is configured to effect an inflow phase or outflow phase encompassing a series of fill-and-measurement or drain-and-measurement steps, each step comprising delivering a predetermined quantity of dialysis fluid to the peritoneal cavity or draining a predetermined quantity of dialysis fluid from the peritoneal cavity and subsequently measuring and recording a pressure value, to establish a function of intraperitoneal pressure by added volume and to use the function to generate and output at least one dialysis therapy-related prediction or recommendation, characterized in that the control unit is configured to obtain an average dwell behavior in terms of temporal variation of interperitoneal volume (IPV) by superimposition of dwell curves of consecutive cycles.

2. The apparatus of claim 1, wherein the control unit is configured to establish a relationship of IPP (Interperitoneal pressure) to IPV (Interperitoneal volume) and to analyze the relationship to obtain prediction parameters for the at least one dialysis therapy-related prediction or recommendation.

3. The apparatus of claim 1, wherein the dialysis therapy-related recommendation is at least one of an optimum filling volume for dialysis fluid in the peritoneal cavity, an optimum dwell time, or an optimum amount of inflow-dwell-outflow cycles.

4. The apparatus of claim 1, wherein the dialysis therapy-related prediction is at least one of an overall therapy time or an ultrafiltration volume.

5. The apparatus of claim 1, wherein the control unit is configured to start the inflow phase after a complete drain of dialysis fluid from the peritoneal cavity.

6. The apparatus of claim 1, wherein the means for cyclically delivering dialysis fluid or enabling gravity flow of dialysis fluid to the peritoneal cavity of a patient comprises at least one pump in case of cyclically delivering.

7. The apparatus of claim 1, wherein the control unit is configured to use a first pressure value determined during a first fill-and-measurement step as an offset and to establish the function of pressure by added volume on the basis of all subsequent pressure values determined during subsequent fill-and-measurement steps or routine, each corrected by subtracting the offset.

8. The apparatus of claim 1, wherein, when effecting fill-and-measurement steps or drain-and-measurement steps, the control unit is configured to deliver or drain the same quantity of dialysis fluid to the peritoneal cavity in all cycles.

9. The apparatus of claim 8, wherein, when effecting the series of fill-and-measurement steps or drain-and-measurement steps, the number of steps in the series is greater than five.

10. The apparatus of claim 8, wherein, when effecting the series of fill-and-measurement steps or drain-and-measurement steps, the number of steps in the series is greater than ten.

11. The apparatus of claim 1, wherein the control unit is configured to consider dynamic pressure measurements by the measurement device obtained during a fluid inflow or outflow in the inflow phase or outflow phase during a continuous routine of fluid inflow or outflow, wherein dynamic pressure measurements are considered to correct pressure values.

12. The apparatus of claim 11, wherein the control unit is configured to temporarily slow down the inflow or outflow when carrying out dynamic pressure measurements by the measurement device.

13. The apparatus of claim 1, wherein the control unit is configured to consider both dynamic pressure measurements and static pressure measurements by the measurement device.

14. The apparatus of claim 1, wherein the measurement device comprises at least one sensor.

15. The apparatus of claim 1, wherein the measurement device comprises a tube which is connected to a patient catheter, wherein a level of dialysis fluid in said tube is an indicator for the intraperitoneal pressure and wherein the measurement device further comprises means to measure said level.

16. The apparatus of claim 1, wherein the control unit is adapted to stop further inflow of dialysis fluid into the peritoneum in case that the intraperitoneal pressure reaches a specific maximum level.

\* \* \* \* \*